United States Patent
Vaquette et al.

(10) Patent No.: US 11,752,002 B2
(45) Date of Patent: Sep. 12, 2023

(54) MULTIPHASIC TISSUE SCAFFOLD CONSTRUCTS

(71) Applicants: Griffith University, Nathan (AU); Queensland University of Technology, Brisbane (AU); Gold Coast Hospital And Health Service, Southport (AU)

(72) Inventors: Cedryck Vaquette, Annerley (AU); Hei Man Hayman Lui, Southport (AU); Saso Ivanovski, Holland Park West (AU); Randy Bindra, Bundall (AU)

(73) Assignees: Griffith University, Nathan (AU); Queensland University of Technology, Brisbane (AU)

(*) Notice: Subject to any disclaimer, the term of this patent is extended or adjusted under 35 U.S.C. 154(b) by 743 days.

(21) Appl. No.: 16/636,706

(22) PCT Filed: Aug. 13, 2018

(86) PCT No.: PCT/AU2018/000133
§ 371 (c)(1),
(2) Date: Feb. 5, 2020

(87) PCT Pub. No.: WO2019/028494
PCT Pub. Date: Feb. 14, 2019

(65) Prior Publication Data
US 2020/0237520 A1    Jul. 30, 2020

(30) Foreign Application Priority Data

Aug. 11, 2017   (AU) ................................ 2017903229

(51) Int. Cl.
*A61F 2/46* (2006.01)
*A61F 2/08* (2006.01)
(Continued)

(52) U.S. Cl.
CPC .............. *A61F 2/4261* (2013.01); *A61F 2/08* (2013.01); *A61L 27/222* (2013.01);
(Continued)

(58) Field of Classification Search
CPC .. A61F 2/08; A61F 2/42; A61F 2/2412; A61L 27/38
See application file for complete search history.

(56) References Cited

U.S. PATENT DOCUMENTS

2010/0310623 A1   12/2010   Laurencin et al.
2011/0066242 A1   3/2011    Lu et al.
(Continued)

FOREIGN PATENT DOCUMENTS

JP    2015-089433    5/2015
WO    2016164566    10/2016

OTHER PUBLICATIONS

Chung et al., "A biodegradable tri-component graft for anterior cruciate ligament reconstruction," Journal of Tissue Engineering and Regenerative Medicine, 11, pp. 704-712 (2014).
(Continued)

*Primary Examiner* — Jason-Dennis N Stewart
(74) *Attorney, Agent, or Firm* — Mintz, Levin, Cohn, Ferris, Glovsky and Popeo, P.C.

(57) ABSTRACT

The present invention relates to a three-dimensional multiphasic synthetic tissue scaffold comprising first, second and third compartments, wherein: each said compartment comprises distinct microstructural, and/or chemical, and/or mechanical properties, and is connected with at least one other compartment of the scaffold via a continuous interface; the tissue scaffold is porous; and the external morphology of the tissue scaffold mimics that of a mammalian joint or a component thereof. The invention further relates to a method for producing the three dimensional multiphasic synthetic
(Continued)

tissue scaffold using a polymeric material, the method comprising using a three-dimensional (3D) bioprinter to print the tissue scaffold by continuously deposit the polymeric material onto a platform until the tissue scaffold is produced in its entirety.

17 Claims, 25 Drawing Sheets

(51) Int. Cl.
*A61F 2/42* (2006.01)
*B33Y 80/00* (2015.01)
*A61L 27/22* (2006.01)
*A61L 27/24* (2006.01)
*A61L 27/38* (2006.01)
*B33Y 10/00* (2015.01)
*A61F 2/30* (2006.01)

(52) U.S. Cl.
CPC ........... *A61L 27/225* (2013.01); *A61L 27/227* (2013.01); *A61L 27/24* (2013.01); *A61L 27/386* (2013.01); *A61L 27/3817* (2013.01); *A61L 27/3821* (2013.01); *A61L 27/3847* (2013.01); *A61L 27/3886* (2013.01); *B33Y 80/00* (2014.12); *A61F 2002/30009* (2013.01); *A61F 2002/30011* (2013.01); *A61F 2002/30062* (2013.01); *A61F 2002/30962* (2013.01); *A61F 2002/30985* (2013.01); *A61F 2002/4289* (2013.01); *A61F 2002/4292* (2013.01); *B33Y 10/00* (2014.12)

(56) References Cited

U.S. PATENT DOCUMENTS

| | | | |
|---|---|---|---|
| 2012/0095482 A1 | 4/2012 | Peterson et al. | |
| 2012/0271418 A1 | 10/2012 | Hollister et al. | |
| 2013/0280303 A1* | 10/2013 | Drapeau | A61P 31/00 424/618 |
| 2013/0282138 A1 | 10/2013 | Schmidt et al. | |
| 2014/0350677 A1 | 11/2014 | Chang et al. | |
| 2016/0106536 A1* | 4/2016 | Chui | A61L 27/18 623/9 |
| 2016/0166727 A1* | 6/2016 | Ganatra | D01F 8/14 521/182 |
| 2018/0296313 A1* | 10/2018 | Mathisen | B32B 5/028 |

OTHER PUBLICATIONS

Criscenti et al., "Triphasic scaffolds for the regeneration of the bone-ligament interface," Biofabrication, 8, pp. 1-13 (2016).

International Search Report and Written Opinion for International Patent Application No. PCT/AU2018/000133 dated Oct. 18, 2018 (14 pages).

Tarafder et al., "Micro-precise spatiotemporal delivery system embedded in 3D printing for complex tissue regeneration," Biofabrication, 8, pp. 1-10 (2016).

Tarafder et al., "Spatiotemporal Delivery of Multiple Growth Factors in 3D Printed Scaffolds for Engineering Integrated Soft Tissue-To-Bone Interfaces From Stem/Progenitor Cells," ORS 2016 Annual Meeting Paper No. 0065, retrieved from the internet on Oct. 16, 2018 (1 page) <https://www.ors.org/Transactions/62/0065.pdf>.

* cited by examiner

A
B

A

B

C

D

E

F

G

H

I

J

MULTIPHASIC TISSUE SCAFFOLD CONSTRUCTS

INCORPORATION BY CROSS-REFERENCE

The present application is a U.S. National Phase Application of PCT International Application No. PCT/AU2018/000133, filed on Aug. 13, 2018 which claims priority from Australian provisional patent application number 2017903229, filed on Aug. 11, 2017 the entire contents of which are incorporated by cross-reference in their entirety.

TECHNICAL FIELD

The present invention relates generally to the field of tissue engineering, and more specifically to tissue engineering scaffolds capable of assisting tissue regeneration. Methods for the production of the scaffolds and their use in regenerating tissue are also provided herein.

BACKGROUND

Tendons and ligaments can fail through trauma or chronic deterioration, and both mechanisms lead to a substantial reduction in musculoskeletal function. Treatments that enhance tendon and ligament repair will have a significant impact on orthopaedic surgery outcomes, reducing repair failures and repeat surgeries, facilitating a more rapid return to function, and lowering health costs. Many current treatments rely on using the patient's own tissue as regenerative scaffolds. This approach is often associated with donor site morbidity, as well as difficulties with size matching, anatomical shape and fixation to bone.

Synthetic scaffolds have been manufactured using a variety of fabrication methods and polymers as an alternative for tendon and ligament repair. However, producing synthetic scaffolds with sufficient strength to withstand normal physiological forces remains challenging, as does replicating existing joint architecture. While synthetic tissue constructs have been used with varying success in larger joints such as the knee (e.g. anterior cruciate ligament repair), very little if any attempts have been made to use synthetic scaffolds in the more difficult environment of small joints. For example, the scapholunate interosseous ligament (SLIL), a C-shaped ligament situated between the scaphoid and lunate carpal bones, is a commonly torn wrist ligament. Injury to this ligament is the most common cause of both static and dynamic carpal instability resulting in conditions such as scapholunate advanced collapse (SLAC) and dorsal intercalated segment instability (DISI). Current surgical options for SLIL tears are suboptimal and these injuries often result in poor prognosis with severe osteoarthritis. Existing tenodesis procedures often fail to restore carpal kinematics. There is no current consensus and no single successful method of SLIL reconstruction as all current methods result in loss of wrist motion with incomplete pain relief, and a second procedure is often needed to remove the screw placed between the bones. In the context of treatments based on autografts poor clinical outcomes are common, most likely originating from inadequate tissue integration of the autograft and/or inappropriate regeneration leading to inferior mechanical properties that are incapable of withstanding the physiological load. A strategy whereby the ligament is fully regenerated and remodeled with strong bony attachments to circumvent the aforementioned issues and improve the success rate of current SLIL reconstruction would be advantageous.

A need exists for synthetic constructs with improved attributes capable of enhancing element/s of tendon and ligament repair, and methods for their production. Preferably, the synthetic constructs produced can be used effectively in small joint repair including, for example, SLIL repair.

SUMMARY OF THE INVENTION

The present invention alleviates at least one of the shortcomings of existing tissue engineering scaffolds and methods for their production.

The bioscaffolds of the present invention are multiphasic and produced in a continuous manner to accurately imitate the morphological characteristics of the tissue to be regenerated. The synthetic scaffold constructs of the present invention may (i) be capable of withstanding normal physiological forces for the integrative and functional repair of soft tissue injuries, and/or (ii) closely mimic existing joint architecture, and/or (iii) allow manipulation to promote vascularization and tissue regeneration, and/or (iv) reduce or eliminate donor morbidity when harvesting autografts.

By way of non-limiting example, the present invention relates at least in part to the following embodiments:

Embodiment 1. A three-dimensional multiphasic synthetic tissue scaffold comprising first, second and third compartments, wherein:

each said compartment comprises distinct microstructural, and/or chemical, and/or mechanical properties, and is connected with at least one other compartment of the scaffold via a continuous interface;

the tissue scaffold is porous; and the external morphology of the tissue scaffold mimics that of a mammalian joint or a component thereof.

Embodiment 2. The multiphasic synthetic tissue scaffold of embodiment 1, wherein any one or more of the first, second and/or third compartments comprises or consists of a series of fibres.

Embodiment 3. The multiphasic synthetic tissue scaffold of embodiment 2, wherein the series of fibres comprises multiple fibre layers.

Embodiment 4. The multiphasic synthetic tissue scaffold of any one of embodiments 1 to 3, wherein the second compartment comprises a series of fibres mimicking the external morphology of a series of ligaments, and said series of fibres are located intermediate to and connecting the first and third compartments.

Embodiment 5. The multiphasic synthetic tissue scaffold of embodiment 4, wherein:

the multiple fibre layers comprise first and second fibre layers, the first fibre layer is aligned along a first axis, the second fibre layer is aligned along a second axis, and the second axis is rotated at an angle relative to the first axis.

Embodiment 6. The multiphasic synthetic tissue scaffold of embodiment 5, wherein the second axis is rotated by an angle of:

at least: 2°, 3°, 4°, 5°, 6°, 7°, 8°, 9°, 10°, 11°, 12°, 13°, 14°, 15°, 16°, 17°, 18°, 19°, or 20° relative to the first axis; or between 20° and 50°, between 25° and 45°, between 30° and 40°, between 25° and 35°, or about 35°, relative to the first axis.

Embodiment 7. The multiphasic synthetic tissue scaffold of embodiment 5 or embodiment 6, wherein the multiple fibre layers comprise a third layer aligned along a third axis, and the third axis is rotated at an angle relative to either or both of the first axis and/or second axis.

Embodiment 8. The multiphasic synthetic tissue scaffold of embodiment 7, wherein the third axis is rotated at an equal or substantially equal angle relative to the first axis and/or second axis.

Embodiment 9. The multiphasic synthetic tissue scaffold of embodiment 7 or embodiment 8, wherein the third axis is rotated in an anticlockwise direction relative to the first axis, and is rotated in a clockwise direction relative to the second axis.

Embodiment 10. The multiphasic synthetic tissue scaffold of any one of embodiments 1 to 9, wherein the external morphology of each of the first and third compartments mimics that of a bone, and the external morphology of the second compartment mimics that of a series of ligaments located intermediate to and connecting the first and third compartments.

Embodiment 11. The multiphasic synthetic tissue scaffold of any one of embodiments 1 to 10, wherein the external morphology of the tissue scaffold mimics that of a scapholunate joint or a component thereof.

Embodiment 12. The multiphasic synthetic tissue scaffold of any one of embodiments 1 to 11, wherein the external morphology of the first compartment mimics that of a scaphoid, the external morphology of the third compartment mimics that of a lunate, and the external morphology of the second compartment mimics that of a series of scapholunate ligaments.

Embodiment 13. The multiphasic synthetic tissue scaffold of embodiment 12, wherein the series of scapholunate ligaments are dorsal scapholunate ligaments, and are not proximal or palmar scapholunate ligaments.

Embodiment 14. The multiphasic synthetic tissue scaffold of embodiment 12 or embodiment 13, wherein the series of scapholunate ligaments are dorsal scapholunate ligaments, and either or both of proximal and/or palmar scapholunate ligaments.

Embodiment 15. The multiphasic synthetic tissue scaffold of any one of embodiments 1 to 14, wherein the scaffold comprises pores with a maximum width of between 100 μM and 1000 μM, between 100 μM and 1000 between 100 μM and 800 μM, between 100 μM and 600 μM, between 200 μM and 600 μM, between 200 μM and 500 μM, between 300 μM and 600 μM, between 300 μM and 500 μM, between 350 μM and 600 μM, between 350 μM and 500 μM, between 400 μM and 600 μM, or between 400 μM and 500 μM.

Embodiment 16. The multiphasic synthetic tissue scaffold of any one of embodiments 1 to 15, further comprising mammalian cells.

Embodiment 17. The multiphasic synthetic tissue scaffold of embodiment 16, wherein the mammalian cells are selected from the group consisting of: ligament-derived stem cells, cartilage stem cells, mesenchymal stem cells (bone marrow stromal cells), adipose-derived stromal cells (e.g. bone-marrow derived mesenchymal stem cells, adipose-derived mesenchymal stem cells), osteoblasts, osteoblast-like cells, stem cells, progenitor cells, or any combination thereof.

Embodiment 18. The multiphasic synthetic tissue scaffold of embodiment 16 or embodiment 17, wherein the cells are human mesenchymal stem cells, or human bone marrow mesenchymal stem cells.

Embodiment 19. The multiphasic synthetic tissue scaffold of any one of embodiments 16 to 18, wherein the mammalian cells are within a cell sheet wrapped around and/or inserted into one or more of the compartments.

Embodiment 20. The multiphasic synthetic tissue scaffold of any one of embodiments 1 to 19, wherein any one or more of the first, second and/or third compartments comprises a polymeric material.

Embodiment 21. The multiphasic synthetic tissue scaffold of embodiment 20, wherein the polymeric material is selected from the group consisting of: collagen, chitosan, hyaluronic acid, alginate, gelatin, polyethylene glycol dimethacrylate (PEG), gelatin methacryloyl, matrigel, fibrinogen, agarose, and polycaprolactone.

Embodiment 22. The multiphasic synthetic tissue scaffold of embodiment 20 or embodiment 21, wherein the polymeric material is polycaprolactone or polyurethane.

Embodiment 23. The multiphasic synthetic tissue scaffold of any one of embodiments 1 to 22, wherein the tissue scaffold is produced using a three-dimensional (3D) bioprinter to continuously deposit the polymeric material onto a platform until the tissue scaffold is produced in its entirety.

Embodiment 24. The multiphasic synthetic tissue scaffold of any one of embodiments 1 to 23, wherein the continuous interface is porous.

Embodiment 25. A method for producing a three dimensional multiphasic synthetic tissue scaffold comprising polymeric material, the method comprising using a three-dimensional (3D) bioprinter to print the tissue scaffold by continuously deposit the polymeric material onto a platform until the tissue scaffold is produced in its entirety, wherein:
the tissue scaffold comprises first, second and third compartments, each said compartment comprises distinct microstructural, and/or chemical, and/or mechanical properties, and each said compartment is connected with at least one other compartment of the scaffold via a continuous interface; and the tissue scaffold is porous and is printed to mimic the external morphology of a mammalian joint or a component thereof.

Embodiment 26. The method of embodiment 25, comprising polymerising the polymeric material to form fibres, wherein the first, second and/or third compartments comprise or consist of a series of said fibres.

Embodiment 27. The method of embodiment 26, wherein the series of fibres are printed to comprise multiple fibre layers.

Embodiment 28. The method of any one of embodiments 25 to 27, wherein the second compartment is printed to comprise a series of fibres mimicking the external morphology of a series of ligaments, and said series of fibres are located intermediate to and connecting the first and third compartments.

Embodiment 29. The method of embodiment 28, wherein:
the multiple fibre layers are printed to comprise first and second fibre layers,
the first fibre layer is aligned along a first axis,
the second fibre layer is aligned along a second axis, and
the second axis is rotated at an angle relative to the first axis.

Embodiment 30. The method of embodiment 29, wherein the second axis is rotated by an angle of:
at least: 2°, 3°, 4°, 5°, 6°, 7°, 8°, 9°, 10°, 11° 12°, 13°, 14°, 15°, 16°, 17°, 18°, 19°, or 20° relative to the first axis; or
between 20° and 50°, between 25° and 45°, between 30° and 40°, between 25° and 35°, or about 35°, relative to the first axis.

Embodiment 31. The method of embodiment 29 or embodiment 30, wherein the multiple fibre layers comprise Embodiment 32. The method of embodiment 31, wherein the third axis is rotated at an equal or substantially equal angle relative to the first axis and/or second axis.

Embodiment 33. The method of embodiment 31 or embodiment 32, wherein the third axis is rotated in an anticlockwise direction relative to the first axis, and is rotated in a clockwise direction relative to the second axis.

Embodiment 34. The method of any one of embodiments 25 to 33, wherein the first and third compartments are printed to mimic the external morphology of a bone, and the second compartment is printed to mimic the external morphology of a series of ligaments located intermediate to and connecting the first and third compartments.

Embodiment 35. The method of embodiment 34, wherein the tissue scaffold is printed to mimic the external morphology of a scapholunate joint or a component thereof.

Embodiment 36. The method of any one of embodiments 25 to 35, wherein the first compartment printed to mimic the external morphology of a scaphoid, the third compartment is printed to mimic the external morphology of a lunate, and the second compartment printed to mimic the external morphology of a series of scapholunate ligaments.

Embodiment 37. The method of embodiment 36, wherein the series of scapholunate ligaments are dorsal scapholunate ligaments, and do not comprise proximal or palmar scapholunate ligaments.

Embodiment 38. The method of embodiment 36, wherein the series of scapholunate ligaments are dorsal scapholunate ligaments, and either or both of proximal and/or palmar scapholunate ligaments.

Embodiment 39. The method of any one of embodiments 25 to 38, wherein the pores have a maximum width of between 100 μM and 1000 μM, between 100 μM and 1000 μM, between 100 μM and 800 μM, between 100 μM and 600 μM, between 200 and 600 μM, between 200 μM and 500 μM, between 300 μM and 600 μM, between 300 μM and 500 μM, between 350 μM and 600 μM, between 350 μM and 500 μM, between 400 μM and 600 μM, or between 400 μM and 500 μM.

Embodiment 40. The method of any one of embodiments 25 to 39, wherein the polymeric material continuously deposited onto the platform to produce the tissue scaffold does not comprise cells.

Embodiment 41. The method of any one of embodiments 25 to 40, further comprising seeding the scaffold with mammalian cells subsequent to producing the scaffold.

Embodiment 42. The method of embodiment 41, wherein the mammalian cells are selected from the group consisting of: ligament-derived stem cells, cartilage stem cells, mesenchymal stem cells (bone marrow stromal cells), adipose-derived stromal cells (e.g. bone-marrow derived mesenchymal stem cells, adipose-derived mesenchymal stem cells), osteoblasts, osteoblast-like cells, stem cells, progenitor cells, or any combination thereof.

Embodiment 43. The method of embodiment 41 or embodiment 42, wherein the cells are human mesenchymal stem cells, or human bone marrow mesenchymal stem cells.

Embodiment 44. The method of any one of embodiments 41 to 43, wherein the seeding comprises wrapping a cell sheet comprising the mammalian cells around, and/or inserting the cell sheet into, one or more of the compartments.

Embodiment 45. The method of any one of embodiments 41 to 44, further comprising transplanting the tissue scaffold into a subject in need thereof.

Embodiment 46. The method of embodiment 45, wherein the mammalian cells are autologous to the subject in need thereof.

Embodiment 47. The method of any one of embodiments 25 to 46, wherein the polymeric material is selected from the group consisting of: collagen, chitosan, hyaluronic acid, alginate, gelatin, polyethylene glycol dimethacrylate (PEG), gelatin methacryloyl, matrigel, fibrinogen, agarose, polyurethane and polycaprolactone.

Embodiment 48. A method for producing the three dimensional multiphasic synthetic tissue scaffold of any one of embodiments 1 to 24, the method comprising using a three-dimensional (3D) bioprinter to continuously deposit polymeric material onto a platform until the tissue scaffold is produced in its entirety.

Embodiment 49. A three dimensional multiphasic synthetic tissue scaffold produced by the method of any one of embodiments 25 to 48.

Embodiment 50. A method for treating an injured ligament in a subject, the method comprising transplanting the three dimensional multiphasic synthetic tissue scaffold of any one embodiments 1 to 24 or 49 into a body compartment of the subject comprising the injured ligament.

Embodiment 51. The method of embodiment 50, wherein the body compartment is a joint.

Embodiment 52. The method of embodiment 50 or embodiment 51, wherein the joint is a scapholunate joint and the ligament is a scapholunate interosseous ligament (SLIL) or a mammalian equivalent thereof.

Embodiment 53. The method of any one of embodiments 50 to 52, wherein the subject is a human.

Embodiment 54. Use of a three dimensional multiphasic synthetic tissue scaffold of any one embodiments 1 to 24 or 49 for the preparation of a medicament for treating an injured ligament in a subject.

Embodiment 55. A three dimensional multiphasic synthetic tissue scaffold of any one embodiments 1 to 24 or 49 for use in treating an injured ligament in a subject.

Embodiment 56. The use of embodiment 54, or the three dimensional multiphasic synthetic tissue scaffold of embodiment 55, wherein the ligament is a scapholunate interosseous ligament or a mammalian equivalent thereof.

Embodiment 57. The use of embodiment 54 or embodiment 56, or the three dimensional multiphasic synthetic tissue scaffold of embodiment 55 or embodiment 56, wherein the subject is a human.

Definitions

As used in this application, the singular form "a", "an" and "the" include plural references unless the context clearly dictates otherwise. For example, the term "polymer" also includes a plurality of polymers.

As used herein, the term "comprising" means "including." Variations of the word "comprising", such as "comprise" and "comprises," have correspondingly varied meanings. Thus, for example, a tissue scaffold construct "comprising" polymer type A may consist exclusively of polymer type A or may include one or more additional components (e.g. polymer type B and/or non-polymer material/s).

As used herein, a "multiphasic" tissue scaffold refers to a tissue scaffold comprising at least two (e.g. two, three, four, five or more) compartments each comprising distinct microstructural, and/or chemical, and/or mechanical properties, as compared to adjacent compartment/s of the scaffold. It will be understood that the compartments of a "multiphasic" tissue scaffold as described herein are produced in a continuous manner (e.g. in the same session of three-dimensional bioprinting), rather than being produced separately then fused and/or joined together.

As used herein, a "synthetic" tissue scaffold is intended to exclude naturally-formed tissue scaffolds and requires that the scaffold is manufactured artificially.

As used herein, reference to a tissue scaffold or tissue scaffold compartment having an "external morphology" that "mimics" a biological component (e.g. a joint, bone, ligament, cartilage) will be understood to mean that the external/outward-facing surface of the tissue scaffold or tissue scaffold compartment is shaped and/or sized to imitate that of the biological component, such that a skilled person in the field would acknowledge the tissue scaffold or tissue scaffold compartment to be representative of the biological component.

As used herein, the term "scapholunate joint" means a joint formed by the scaphoid bone, the scapholunate ligament and the lunate bone.

As used herein, the term "subject" includes any animal of economic, social or research importance including bovine, equine, ovine, primate, avian and rodent species. Hence, a "subject" may be a mammal such as, for example, a human or a non-human mammal.

As used herein, the term "about" when used in reference to a recited numerical value includes the recited numerical value and numerical values within plus or minus ten percent of the recited value.

As used herein, the term "between" when used in reference to a range of numerical values encompasses the numerical values at each endpoint of the range. For example, a polypeptide of between 10 residues and 20 residues in length is inclusive of a polypeptide of 10 residues in length and a polypeptide of 20 residues in length.

Any description of prior art documents herein, or statements herein derived from or based on those documents, is not an admission that the documents or derived statements are part of the common general knowledge of the relevant art.

For the purposes of description, all documents referred to herein are hereby incorporated by reference in their entirety unless otherwise stated.

BRIEF DESCRIPTION OF THE FIGURES

Preferred embodiments of the present invention will now be described by way of example only, with reference to the accompanying FIGS. 1-31 wherein.

DETAILED DESCRIPTION

Figure 1:
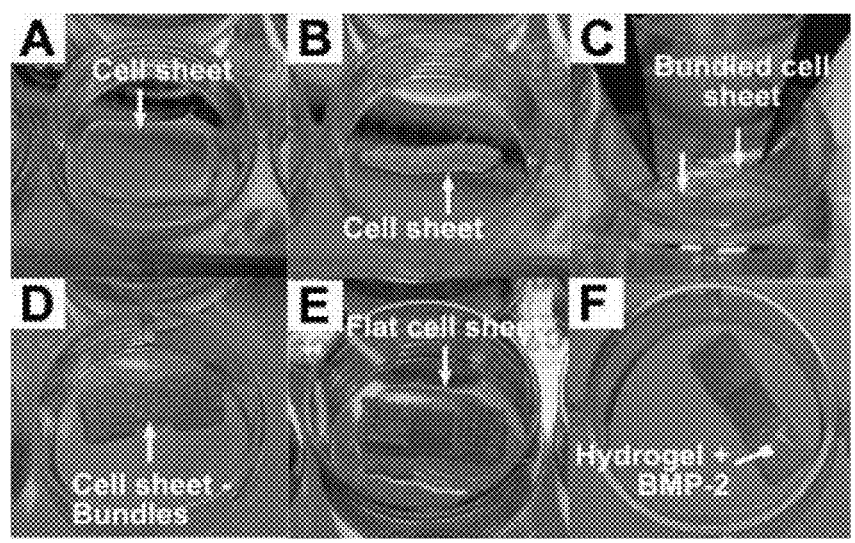
FIG. 1 shows the process of harvesting of human bmMSC cell sheets and seeding into BLB scaffolds. A) Sterile tweezers were used to gently scrape the outer edge of cell sheet and detach it from the walls of the well. B) The cell sheet was rolled towards the centre of the well using the tweezers and folded in order to form a bundle. C-D) Four cell sheet bundles were seeded in between the ligament strands of the PCL scaffold (with dorsal surface facing upwards). E) The scaffold (with dorsal surface facing down) was placed on the fifth cell sheet which was wrapped around the bone and ligament compartments. F) 25 µL of the hydrogel was carefully dispensed into the bone compartment.

The present invention provides synthetic and biocompatible scaffolds for surgical application in joint and/or ligament repair.

These multiphasic bioscaffolds with strategic biomimicry can allow for integrative and functional repair of soft tissue injuries in a manner that is superior to equivalent autografts due to factors including: (i) the capacity to more closely replicate the external morphology of the tissue under treatment allowing for identical/near identical matching of the scaffolds to existing joint architecture; and/or (ii) the maintenance of equivalent biomechanical properties as the native joint and/or ligament; and/or (iii) the capacity for manipulation to promote vascularisation and tissue regeneration thereby minimising overall healing time; and/or (iv) elimination of donor morbidity when harvesting autografts.

The present invention relates to these scaffolds, methods for their production, and their use in tissue repair (e.g. joint and/or ligament repair). The various features of the invention described below should not be considered limiting unless the context clearly indicates that to be the case.

Polymers

The present invention provides scaffolds constructed from polymers and methods for their production.

Without placing any particular limitation on the type of polymers that may be used in a method or scaffold of the present invention, certain characteristics may be desirable. For example, the polymers may be biocompatible (i.e. non-toxic), non-immunogenic, have a capacity to act as adhesive substrates for cells, promote cell growth, and/or allow the retention of differentiated cell function.

Additionally or alternatively, the polymers may comprise one or more physical characteristics allowing for mechanical strength, large surface to volume ratios, and/or straightforward processing into desired shape configurations.

A scaffold constructed from a polymer in accordance with the methods of the invention may be rigid enough to maintain the desired shape under in vivo conditions.

A polymer used in a method or construct of the present invention may be biodegradable or substantially biodegradable. Preferably, the degraded products of the polymer are biocompatible.

Alternatively, a polymer used in a method or construct of the present invention may be a non-degradable polymer. Without limitation, suitable non-degradable polymer materials that may be used include poly(ethylene terephthalate) (PET), Polyether ether ketone (PEEK), and combinations thereof.

The polymer may be a homopolymer or a copolymer.

The polymer may be synthetic or natural.

Non-limiting examples of potentially suitable synthetic polymers include polyesters (e.g. Poly(glycolic acid), Poly (l-lactic acid), Poly(d,l-lactic acid), Poly(d,l-lactic-co-glycolic acid), Poly(caprolactone), Poly(propylene fumarate), poly (p-dioxanone), poly (trimethylene carbonate), and their copolymers, polyanhydrides (e.g. Poly [1,6-bis(carboxyphenoxy) hexane]), Poly(phosphoesters) (e.g. poly(bis(hydroxyethyl), terephthalate-ethyl, ortho-phosphate/terephthaloyl chloride), poly(ortho esters) (e.g. Alzmer®), polycarbonates (e.g. Tyrosine-derived polycarbonate), polyurethanes (e.g. Polyurethane based on LDI and poly(glycolide-co-γ-caprolactone)), and polyphosphazenes (e.g. ethylglycinate polyphosphazene).

Non-limiting examples of potentially suitable natural polymers include those derived from proteins such as collagen, fibrin, gelatin, albumin and polysaccharides such as cellulose, hyaluronate, chitin, glycosaminoglycans (e.g. hyaluronic acid), proteoglycans (e.g. chondroitin sulphate, heparin), fibronectin, laminin, and alginate.

In certain embodiments, the polymer may comprise proteins. The proteins may be fibrillar proteins. Non-limiting examples of suitable fibrillar proteins include collagen, elastin, fibrinogen, fibrin, albumin and gelatin.

A polymer used in a method or scaffold of the present invention may exist as a polymer in its natural state. Such polymers may be further polymerised and/or cross-linked with other polymers.

Additionally or alternatively, a polymer used in a method or scaffold of the present invention may be prepared from monomer units using any suitable technique known in the art. Polymer chains may also be further polymerised by the addition of further monomer unit(s) and/or by linking with other polymer chains.

In certain embodiments, monomer units and/or separate polymer chains may be linked together using a suitable polymerising agent. Polymerisation agents and methods for their use are well known to those of skill in the art. Non-limiting examples of potentially suitable polymerisation agents include diisocyanates, peroxides, diimides, diols, triols, epoxides, cyanoacrylates, enzymes (e.g. polymerases) and the like.

A polymer used in a method or scaffold of the present invention may be cross-linked to form a polymer network. The polymer networks may be two-dimensional or three-dimensional. Potentially suitable cross-linking agents include, but are not limited to, genipin, glutaraldehyde, carbodiimides (e.g. EDC), imidoesters (e.g. dimethyl suberimidate), N-Hydroxysuccinimide-esters (e.g. BS3), divinyl sulfone, epoxides, imidazole, sugars (e.g. pentoses or hexoses).

By way of non-limiting example only, a fibrin polymer may be formed from fibrinogen monomer precursors in the presence of a serine protease (e.g. thrombin) to initiate the spontaneous aggregation of fibrin monomers into a nanofibrous network. Calcium ions and factor XIII (a transglutaminase) may then be used to covalently crosslink the fibrin polymers.

A polymer used in a method or scaffold of the present invention may be a "photopolymer". As used herein, the term "photopolymer" encompasses a polymer, and monomer units capable of assembling into a polymer, that can be made to polymerise and/or cross-link, upon exposure to a form of electromagnetic radiation (e.g. infrared light, visible light, ultraviolet light, X-rays, gamma rays). The polymerizing and/or cross-linking may occur spontaneously upon exposure to electromagnetic radiation, or may require (or be enhanced by) the presence of one or more additional compounds (e.g. a catalyst, or a photoinitiator).

Any type of photopolymer may be used in a method or scaffold of the present invention. Suitable photopolymers may include, but are not limited to, resins (e.g. epoxy resins, acrylate resins, Accura® SI 10), dimethacrylate polymers, poly(propylene fumarate) (PPF), blends of PPF and diethyl fumarate (DEF), photopolymerized poly(ethylene glycol) (PEG), 2-hydroxyethyl methacrylate (HEMA), poly(ethylene glycol) diacrylate (PEGDA), and the like.

A photopolymer used in a method or scaffold of the present invention may be induced to polymerize, cross-link and/or cure in the presence of a photoinitiator. As used herein, a "photoinitiator" is a molecule that upon absorption of light at a specific wavelength produces one or more reactive species capable of catalysing polymerization, cross-linking and/or curing reactions. For example, the photoinitiator may be water-compatible and act on molecules containing an acrylate or styrene group (e.g. Irgacure 2959, 184, and 651; VA-086; or V-50). The photoinitiator may be a chromophore. Other non-limiting examples of suitable photoinitiators include ruthenium II trisbipyridyl chloride [RuII (bpy)$_3$]$^{2+}$, 2,2-dimethoxy-2-phenyl acetophenone (Irgacure 651) and 2-photon sensitive chromophore (AF240).

Tissue Scaffolds

Scaffolds according to the present invention are synthetic and may be designed to mimic properties of biological tissue (e.g. mammalian tissue, human tissue). As noted above, they may be produced using polymers.

The scaffolds may be multiphasic meaning that they may comprise multiple compartments having distinct microstructural, and/or chemical, and/or mechanical properties, as compared to adjacent compartment/s in the scaffold. Accordingly, the scaffolds may comprise two, three, four, five or more than five individual compartments. Individual compartments of the scaffolds may be manufactured in a continuous fashion manner such that the entire scaffold including all of its compartments is generated as a single unit rather than producing series of individual compartments and subsequently joining, fusing or connecting them together to form the complete scaffold.

In some embodiments of the present invention, the multiphasic scaffolds comprise compartment/s that mimic the external morphology of a joint or a component of a joint (e.g. ligament, bone, cartilage, and combinations thereof). The joint may be a mammalian joint (e.g. a human joint). Non-limiting examples of joints include fibrous joints (e.g. sutures, gomphosis, syndesmosis), cartiliginous joints (e.g. synchrondosis, symphysis), and synovial joints (e.g. gliding, hinge, pivot, condyloid, saddle, ball and socket). Accordingly, in some embodiments the joint may be an invertebral joint (e.g. an intervertebral cartilaginous joint, an intervertebral synovial facet joint, a zygapophysial joint), an atlantoaxial joint, an elbow joint, a finger or thumb joint (e.g. interphalangeal joint, metacarpophalangeal joint, proximal interphalangeal joint, distal interphalangeal joint), a forearm joint (e.g. a proximal radioulnar joint, a distal radioulnar joint), a hip joint, a shoulder joint (e.g. a glenohumeral joint, a sternoclavicular joint, an acromioclavicular joint) or a wrist joint (e.g. a radiocarpal joint, intercarpal joint, midcarpal joint, carpometacarpal joint, an intermetacarpal joint). The multiphasic scaffolds may comprise compartment/s that mimic the external morphology of component/s (e.g. ligament/s, bone/s, cartilage/s) of the joints. The skilled addressee is well aware of the various components of joints within mammalian (e.g. human) subjects which are well characterised in the literature (see, by way of non-limiting example, Marieb and Hoehn, Human Anatomy and Physiology (10$^{th}$ Addition); Harris, Mammal Anatomy, an illustrated guide, 2010, Marshall Cavendish; Jacob, Human Anatomy: A Clinically Oriented Approach, 2007, Elsevier; Dimon Rr, Anatomy of the Moving Bod (2$^{nd}$ edition), 2012, North Atlantic Books; Agur and Dalley, Grant's Atlas of Anatomy (12$^{th}$ edition), 2009, Wolters Kluwer/Lippincott Williams & Wilkins).

Non limiting examples of the multiphasic scaffolds include those which comprise, in sequence, bone-ligament compartments, ligament-bone compartments, bone-ligament-bone compartments, bone-cartilage compartments, cartilage-bone compartments, bone-cartilage-bone compartments, muscle-tendon compartments, tendon-bone compartments, and muscle-tendon-bone compartments.

Again without limitation, the multiphasic scaffold may mimic the external morphology of scapholunate interosseous ligaments, scapholunate interosseous ligaments in connection with a scaphoid, scapholunate interosseous ligaments in connection with a lunate, or scapholunate interosseous ligaments with first ends in connection with a scaphoid and a second ends in connection with a lunate. The scapholonate interosseous ligaments may include dorsal (back), and/or proximal (intermediate, interosseous), and/or palmar (front, volar) ligaments.

The scaffolds of the present invention may be porous. The porosity of the scaffold is preferably of a size that allows the migration of components (e.g. cells, proteins, growth factors, nutrients, and/or cellular wastes) within and/or through the scaffold. In some embodiments, the constructs may comprise pores of between about 100 µM and about 1000 µM in width or diameter, between about 100 µM and about 900 µM in width or diameter, between about 100 µM and about 800 µM in width or diameter, between about 100 µM and about 700 µM in width or diameter, between about 100 µM and about 600 µM in width or diameter, less than about 800 µM in width or diameter, or less than about 700 µM, 600 µM, 500 µM, 400 µM, 300 µM, 200 µM, 100 µM, or 50 µM in width or diameter. In some embodiments, the constructs may comprise substantially circular pores of less than about 800 µM in diameter, or less than about 700 µM, 600 µM, 500 µM, 400 µM, 300 µM, 200 µM, 100 µM, or 50 µM in diameter.

Bioprinting

Scaffolds according to the present invention may be produced using a suitable bioprinting technique. Preferably, the bioprinting technique is a three-dimensional bioprinting technique.

Non-limiting examples of suitable bioprinting techniques include inkjet-based bioprinting (e.g. thermal inkjet bioprinting, piezoelectric inkjet bioprinting) in which droplets bioink are generated at a nozzle by a thermal or piezoelectric actuator, pressure-assisted bioprinting (e.g. microextrusion) in which biomaterials are extruded under pressure (e.g. by screw- or plunger-based pressure or pneumatic pressure) thorough a microscale nozzle or a microneedle onto a substrate and may be used to fabricate three-dimensional scaffolds layer by layer, laser-assisted bioprinting (e.g. laser scanning photolithography, two-photon laser scanning photolithography) in which a laser is used as an energy source to deposit biomaterials onto a substrate and fabricate the scaffold, and stereolithography in which patterned light is used to polymerize a liquid photopolymer selectively, layer by layer.

Persons skilled in the art are well aware of these and other suitable bioprinting techniques that can be used in the methods of the present invention. By way of example only, reference is made to publications by Boland et al. Biotechnol J. 2006 Sep. 1(9):910-7; Chia and Wu, J Biol Eng. 2015; 9:4; Irvine and Venkatraman, Molecules 2016, 21, 1188; Jana and Lerman, Biotechnol Adv. 2015 December; 33(8):1503-21; Li et al. J Transl Med. 2016; 14: 271; Melchels, et al. Progr. Polymer Sci. 37(8) 2012: 1079-1104; Murphy and Atala Nat. Biotechnol. 32(8) 2014: 773-785; Skardal A. Bioprinting Essentials of Cell and Protein Viability. Essentials of 3D Biofabrication and Translation. Atala A, Yoo J J, Eds. Academic Press: Cambridge, Mass., January 2015: 1-17; and Wang et al. Biofabrication. 2015 Dec. 22; 7(4): 045009. The Examples of the present application also provide an exemplary bioprinting technique that can be used to produce a scaffold according to the present invention.

The present invention contemplates the use of "CAD" (computer-aided design) to assist in generating the scaffold constructs described herein. As used herein, the term "CAD" includes all manner of computer aided design systems, including pure CAD systems, CAD/CAM systems, and the like, provided that such systems are used at least in part to develop or process a model of a three-dimensional scaffold construct of the present invention. Non-limiting examples include Solidworks (Solidworks Corp.) and LSM software (Zeiss).

Cell Seeding

The scaffolds of the present invention may be seeded with cells. While no particular limitation exists as to the particular type/s of cells that may be used to seed the scaffolds, it is envisaged that the inclusion of stem cells and/or precursor cells capable of differentiating into cells type/s within the tissue of interest (i.e. the tissue that the scaffold seeks to mimic). By way of no-limiting examples only, the stem cells and/or precursor cells may be capable of differentiating into any one or more of mesenchymal osteoprogenitor cells, osteoblasts, osteocytes, osteoclasts, chondrocytes, and chondrocyte progenitor cells.

For example, scaffolds comprising one or more compartment/s mimicking a bone may be seeded with any cell that is capable of differentiating or expanding into an osteoblast cell. For example, mesenchymal stem cells (bone marrow stromal cells) and/or adipose-derived stromal cells (e.g. bone-marrow derived mesenchymal stem cells, adipose-derived mesenchymal stem cells) may be used for this purpose.

Scaffolds comprising one or more compartment/s mimicking cartilage may be seeded with any cell that is capable of differentiating or expanding into a cartilage cell. For example, cartilage stem cells, mesenchymal stem cells, (bone marrow stromal cells) and/or adipose-derived stromal cells (e.g. bone-marrow derived mesenchymal stem cells, adipose-derived mesenchymal stem cells) may be used for this purpose.

Scaffolds comprising one or more compartment/s mimicking ligament/s may be seeded with any cell that is capable of differentiating or expanding into a ligament cell. For example, ligament-derived stem cells, mesenchymal stem cells, (bone marrow stromal cells) and/or adipose-derived stromal cells (e.g. bone-marrow derived mesenchymal stem cells, adipose-derived mesenchymal stem cells) may be used for this purpose.

Other non-limiting cell types that may be used to seed the scaffolds described herein include chord blood stem cells, embryonic stem cells, induced pluripotent stem cells, adult stem cells, blast cells, cloned cells, and/or placental cells.

Other non-limiting of examples of cell types that may be used to seed the scaffolds described herein include any cell as mesenchymal osteoprogenitor cells, osteoblasts, osteocytes, osteoclasts, chondrocytes, and chondrocyte progenitor cells. Preferably the cells are from a compatible human donor. More preferably, the cells are from the patient (i.e., autologous cells).

No limitation exists as to the timing or methodology used to seed the scaffolds.

Accordingly, in some embodiments the cells are seeded during the construction of the scaffold itself. For example, the cells can be included in or mixed with the material used to fabricate the scaffold (e.g. in a liquid mixture of polymeric material and cells). In embodiments where cells are included in or mixed with the bioprinting material the resulting construct may be cellularized with, for example, cells distributed throughout, cells distributed in specific compartment/s, and/or different cell types placed and/or orientated to mimic the desired natural tissue.

In other embodiments, the scaffold may be produced independently of the cells which can be seeded subsequently. For example, the cells may be placed in an appropriate culture medium and the scaffold placed in the medium to facilitate seeding of the scaffold. Various techniques of enhancing cell seeding in this context are known in to those skilled in the art, and may involve manual shaking, techniques to concentrate the cells, the addition of cell growth, differentiation and/or adhesion factors, and the like.

In some embodiments of the present invention, preformed multiphasic scaffolds may be seeded using cell sheet technology. Cell sheet technology is known to those of skill in the art. By way of non-limiting example only, reference is made to Costa et al. Journal of clinical periodontology. 2014; 41(3):283-94; Neo et al. Connect Tissue Res. 2016: 1-15; Yamato and Okano, 2004, Today 7, 42-47; Yang et al. 2005, Biomaterials 26, 6415-6422). Cell sheets may thus be prepared, harvested, and placed within and/or wrapped around a pre-prepared scaffold of the present invention. The application/seeding of cell sheets into and/or around tissue scaffolds can be performed using methods similar to those described in, for example, Carter et al. Ann Biomed Eng. 2017; 45(1): 12-22.

The number of cells used to seed a given scaffold construct will generally depend on factors such as the dimensions of the construct along with the size and morphology of the cells utilised. Preferably, the scaffold constructs comprise a high density of cells, although the density of cells will depend on the particular application.

In certain embodiments, the scaffold may be seeded with between about 50 million and 200 million cells/ml, between about 100 million and 200 million cells/ml, between about 100 million and 150 million cells/ml, between about 1 million cells/ml and about 50 million cells/ml, or between about 1 million cells/ml and about 10 million cells/ml.

The scaffolds may additionally comprise other bioactive components. Non-limiting examples of bioactive components include proteins (e.g. extracellular matrix proteins such as collagen, elastin, pikachurin; cytoskeletal proteins such as actin, keratin, myosin, tubulin, spectrin; plasma proteins such as serum albumin; cell adhesion proteins such as cadherin, integrin, selectin, NCAM; and enzymes); neurotransmitters (e.g. serotonin, dopamine, epinephrine, norepinephrine, acetylcholine); angiogenic factors (e.g. angiopoietins, fibroblast growth factor, bone growth factors such as bone morphogenic protein (e.g. BMP-2), cartilage growth factors, ligament growth factors, meniscus growth factors, vascular endothelial growth factor, matrix metalloproteinase enzymes); amino acids; galactose ligands; nucleic acids (e.g. DNA, RNA); drugs (antibiotics, anti-inflammatories, antithrombotics, and the like); polysaccharides; proteoglycans; hyaluronate; cross-linkers such as factor XIII; lysyloxidase; anticoagulants; antioxidants; cytokines (e.g. interferons (IFN), tumor necrosis factors (TNF), interleukins, colony stimulating factors (CSFs)); hormones or growth factors (e.g. insulin, insulin-like growth factor, epidermal growth factor, oxytocin, osteogenic factor extract (OFE), epidermal growth factor (EGF), transforming growth factor (TGF) (e.g. TGF-β proteins including bone morphogenetic protein 2, platelet derived growth factor (PDGF-AA, PDGF-AB, PDGF-BB), acidic fibroblast growth factor (FGF), basic FGF, connective tissue activating peptides (CTAP), thromboglobulin, erythropoietin (EPO), and nerve growth factor (NGF)); or combinations thereof.

The additional bioactive components may be obtained from any source (e.g. humans, other animals, microorganisms). For example, they may be produced by recombinant means or may be extracted and purified directly from a natural source.

Treatments

The scaffolds of the present invention may be used in the regeneration and/or repair of damaged tissue in a subject. A skilled person in the art will readily recognise that the scaffolds described herein can be bioprinted in a manner designed to mimic a broad number of mammalian (e.g. human) tissues including, for example, those comprising any one or more of bone, cartilage and/or ligament, in any combination.

In accordance with the treatment methods of the present invention, the scaffolds can be transplanted into a subject in need thereof, at the tissue site requiring repair and/or regeneration.

Non-limiting examples of tissues that may be treated in accordance with the methods of the present invention include a joint or a component of a joint (e.g. ligament, bone, cartilage, and combinations thereof). The joint may be a mammalian joint (e.g. a human joint).

Non-limiting examples of joints that may be treated in accordance with the methods of the present invention include fibrous joints (e.g. sutures, gomphosis, syndesmosis), cartiliginous joints (e.g. synchrondosis, symphysis, meniscus), and synovial joints (e.g. gliding, hinge, pivot, condyloid, saddle, ball and socket). Accordingly, in some embodiments the joint may be an invertebral joint (e.g. an intervertebral cartilaginous joint, an intervertebral synovial facet joint, a zygapophysial joint), an atlantoaxial joint, an elbow joint, a finger or thumb joint (e.g. interphalangeal joint, metacarpophalangeal joint, proximal interphalangeal joint, distal interphalangeal joint), a forearm joint (e.g. a proximal radioulnar joint, a distal radioulnar joint), a hip joint, a shoulder joint (e.g. a glenohumeral joint, a sternoclavicular joint, an acromioclavicular joint) or a wrist joint (e.g. a radiocarpal joint, intercarpal joint, midcarpal joint, carpometacarpal joint, an intermetacarpal joint). Individual components (e.g. ligament/s, bone/s, cartilage/s) of the joints may also be targeted by the treatment methods. The skilled addressee is well aware of the various components of joints within mammalian (e.g. human) subjects which are well characterised in the literature (see, by way of non-limiting example, Marieb and Hoehn, Human Anatomy and Physiology ($10^{th}$ Addition); Harris, Mammal Anatomy, an illustrated guide, 2010, Marshall Cavendish; Jacob, Human Anatomy: A Clinically Oriented Approach, 2007, Elsevier; Dimon Rr, Anatomy of the Moving Bod ($2^{nd}$ edition), 2012, North Atlantic Books; Agur and Dalley, Grant's Atlas of Anatomy ($12^{th}$ edition), 2009, Wolters Kluwer/Lippincott Williams & Wilkins).

In accordance with the treatment methods of the present invention, the scaffolds can be transplanted into a subject in need thereof, at the tissue site requiring repair and/or regeneration.

The cells seeded in the scaffolds utilised for transplantation may be sourced from a compatible human donor, or from the subject him/herself (i.e. autologous cells). The subject may be any animal of economic, social or research importance including bovine, equine, ovine, primate, avian and rodent species. Accordingly, the subject may be a mammal such as, for example, a human or a non-human mammal.

It will be appreciated by persons of ordinary skill in the art that numerous variations and/or modifications can be made to the present invention as disclosed in the specific embodiments without departing from the spirit or scope of the present invention as broadly described. The present embodiments are, therefore, to be considered in all respects as illustrative and not restrictive.

EXAMPLES

The present invention will now be described with reference to specific Example(s), which should not be construed as in any way limiting.

Example One: Additively Manufactured Multiphasic Bone-Ligament-Bone Scaffold for Scapholunate Interosseous Ligament Reconstruction Overview (i) Aim The scapholunate interosseous ligament (SLIL) is a commonly torn wrist ligament. Current surgical options for SLIL tears are suboptimal and these injuries alter carpal kinematics resulting in secondary osteoarthritis. This research aims to develop a novel multiphasic bone-ligament-bone (BLB) scaffold using 3D-printing and cell sheet technology for the reconstruction of the dorsal scapholunate interosseous ligament (SLIL).

(ii) Methodology

Multiphasic bone-ligament-bone scaffolds modelled from the dorsal component of the SLIL were 3D-printed with medical grade polycaprolactone (PCL). These comprised two bone compartments bridged by aligned PCL fibres mimicking the architecture of the native ligament.

(iii) Results

Mechanical testing of the BLB scaffolds showed that they were capable of withstanding physiological forces. The BLB construct was implanted ectopically into athymic rats and harvested at 2 and 8 weeks. Three experimental groups were utilised (i) BLB scaffold only control, (ii) bone morphogenetic protein (BMP) in the bone compartment of the BLB scaffold and (iii) BMP in the bone compartment and human cell sheets in the ligament of the BLB scaffold. The cell sheets were formed by culturing human bone marrow mesenchymal stem cells on tissue culture plastic for 21 days with or without ascorbic acid supplemented media. Cell sheets treated with ascorbic acid showed high DNA content and ECM deposition in vitro prior to implantation, and was therefore used for subsequent experiments. Analysis of cell sheets in vitro showed that harvesting and placement of cell sheets did not compromise cell viability and that the sheets were homogeneously distributed into the ligament compartment prior to implantation. Histological analysis of the in vivo samples demonstrated that the scaffolds were biocompatible, displayed good tissue integration and were highly vascularized. Bone formation was observed only at week 8 time-point and remained localised to the bone compartment. Cells in the ligament compartment were aligned and the graft underwent extensive tissue remodelling in vivo.

(iv) Conclusion

This proof-of-concept study demonstrated that a 3D-printed multiphasic bone-ligament-bone scaffold can be successfully generated and implanted in a predictable manner for application in scapholunate ligament reconstruction. The specific architecture of the scaffold provided guiding properties for ligament fibre alignment and tissue regeneration.

Materials and Methods (i) Bone-Ligament-Bone Scaffold Manufacturing

Medical-grade polycaprolactone (mPCL, 80 kDa) was purchased from Corbion. Additively manufactured BLB mPCL scaffolds were designed comprising of two bone compartments bridged by aligned mPCL fibres (ligament compartment) mimicking the architecture and organisation of the native ligament. Two designs comprising of a 350 µm and 600 µm fibre interdistance in the ligament compartment were generated for physical characterisation, in vitro testing and ectopic implantation. The mPCL 3D scaffolds were fabricated using an in-house bioextruder under the following conditions: the mPCL was placed in a stainless reservoir and heated at 110° C. through a heated cartridge unit and extruded through a 22 G needle to deposit mPCL fibres on a programmable stage. Continuous printing process resulted in fabrication of properly connected fibres forming a construction with 0/90° between layers (in the bone compartment) and a 0/0° arrangement in the ligament compartment (aligned fibres) with a layer thickness of 300 µm. This resulted in the production of individual scaffolds having an elongated U-shape whereby the bone compartments had a dimension of 5×5×10 mm3 and were bridged by the ligament compartment with a dimension of 5 mm long, 5 mm wide and 3 mm high. These BLB scaffolds were utilized as such for the rest of the study, except for tensile testings where BLB rectangular scaffolds of 15×5×3 mm$^3$, still featuring the 5 mm long bone compartments and a 5 mm long ligament compartment, were used due to experimental requirements.

(ii) BLB-Morphology and Porosity

The morphology of the scaffold was investigated using Scanning Electron Microscopy (SEM). SEM was conducted at the Centre of Analytical Research Facility (CARF) using a QUANTA200 microscope. The mPCL scaffolds were sputter coated with gold for 150 seconds prior to visualisation under the microscope (EHT=10 kV). The morphology along with the porosity of the scaffold (n=6) were investigated using microcomputed tomography (µCT). The 350 and 600 µm BLB-scaffolds were analysed using a µCT40 (SCANCO Medical AG, Brüttisellen, Switzerland) with a voltage of 55 kVp, a current of 120 µA, and power of 8 W, an integration time of 300 ms and a voxel size of 20 µm. 3D images were reconstructed using the µCT software.

(iii) Mechanical Testing

Tensile Testing and Cyclic Testing

In preparation for mechanical testing, the bone compartments were carefully filled with a fast setting epoxy resin (Selleys Araldite 5 Minute, Australia) to stiffen the bone compartments before being subsequently inserted in pneumatic grips. This prevented irreversible compression and stress concentration at the ligament-bone compartment interface. Care was taken to ensure that the resin remained contained in the bone compartments and that there was no contact with the ligament fibres. The specimens were dried overnight at room temperature. The sample was placed into the grips, ensuring that the ligament fibres were parallel to the longitudinal axis of the grips. The tensile mechanical properties of the construct were measured using a 5848 Instron microtester fitted with a 500N load cell and a cross-head speed of 20 mm·min-1 at room temperature. Five replicate samples were tested for each design and the linear stiffness (calculated from the initial linear part of the F/elongation curve), the yield force and the ultimate force and strain were calculated. Cyclic testing was performed in PBS at 37° C. by applying a preload of 0.1 N. The samples were then subjected to 1,000 continuous cycles at a frequency of 0.5 Hz in the range of 0-5% or 0-10% strain. The evolution of the stiffness and the force at peak were measured and plotted as a function of cycle number.

Compressive Test

The bone compartments of the 350 µm and 600 µm designs were printed and cut into 5×5 mm² squares. The compressive properties were assessed using a 5848 Instron microtester fitted with a 500N load cell and at a cross-head speed of 0.5 mm·min-1 at room temperature. The compressive modulus was determined form the initial linear curve of the stress versus strain curve (n=5).

(iv) Cell Culture and Generation of Cell Sheet (CS)

Human bone marrow mesenchymal stem cells (bmMSCs) (PT-2501, Lonza Australia, Mt Waverley, VIC) between passages 5 and 7 were used in this experiment. Cell culture media was a combination of Dulbecco's modified Eagle's medium (DMEM, Gibco) with 10% foetal bovine serum, 1% Penicillin Streptomycin (Gibco), MEM Non-essential Amino acids (Gibco) and with or without 100 µg/mL of L-ascorbic acid 2-phosphate (Sigma-Aldrich). To generate the cell sheet, bmMSCs were seeded at 40,000 cells per well in a 12-well plate and cultured in ascorbic acid supplemented media for 21 days (at 37° C., 5% CO2). At this time point, the mature cell sheets visibly retracted from the wall of the well. For comparison purposes, cells were also cultured in expansion media (Dulbecco's modified Eagle's medium (DMEM, Gibco) with 10% fetal bovine serum, 1% Penicillin Streptomycin (Gibco) with additional MEM non-essential amino acids). The media was changed every 2 days. At 21 days, the samples were utilised for the various experiments: they were either fixed with 4% paraformaldehyde for immunofluorescence, frozen at −80° C. for DNA and collagen quantification, or immediately harvested for live dead analysis or used for seeding the scaffolds prior to ectopic implantation.

(v) Cell Sheet Characterisation

DNA and Collagen Quantification

DNA quantification was conducted as per protocol using the Quant-iT™ PicoGreen® dsDNA kit (Invitrogen) (n=6 for each group). Fluorescence of samples was measured using a fluorescence plate reader (BMG POLARstar Omega, Ottenberg, Germany) at excitation wavelength of 480 nm and emission wavelengths of 480 nm and 520 nm. Similarly, collagen quantification was conducted as per protocol using the Hydroxyproline Colorimetric Assay Kit (Biovision) (n=6 for each group). Absorbance of samples was evaluated using a plate reader (BMG POLARstar Omega, Ottenberg, Germany) at a wavelength of 560 nm Immunofluorescence Immunofluorescence staining was conducted to assess the morphology and quantity of extracellular matrix in the samples (n=3 per stain). Cell sheets were incubated with 1% BSA, 22.52 mg/mL glycine in PBST for 30 minutes to block unspecific binding of antibodies. Primary antibodies for collagen 1a (Santa Cruz Biotechnology; 1:250), collagen III (Abcam; 1:200), elastin (Abcam; 1:200), tenascin C (Abcam; 1:500) and aggrecan (Abcam; 1:50) were diluted accordingly in 1% BSA and samples were incubated at 4° C. overnight. Samples were rinsed three times with PBS and further incubated with the respective secondary antibody (1:200; Invitrogen, goat anti-mouse IgG alexa fluor, Santa Cruz Biotechnology, goat anti-rabbit PE) for 30 minutes. They were then counterstained with HOECHST (ThermoFischer; 1:1000) before being visualized using confocal microscopy (Nikon AR1+ Confocal Machine) using 405 nm, 488 nm and 561 nm wavelengths.

SEM

SEM was conducted using the same method as described above. The cellularised scaffolds (n=3 per design) were processed as per standard protocol involving osmium tetroxide infiltration, dehydration and Hexamethyldisilazane immersion prior to final drying at room temperature. Similarly to the above described method, the BLB-scaffolds were sputter coated with gold for 150 seconds prior to visualisation under the microscope (EHT=5 kV).

(vi) Scaffold In Vitro Characterisation

Scaffold Preparation and Sterilisation

Firstly, scaffolds were etched by immersion in 5M NaOH at 37° C. for 30 minutes before being washed three times (5 minute duration) with distilled H2O. Secondly, the scaffolds were incubated in 100% ethanol at room temperature for 30 minutes before being sterilised under UV light for 30 minutes.

Cell Sheet Harvesting

Five cell sheets cultured with ascorbic acid (100 µg/mL) were utilised to cellularise the BLB scaffold according to the following protocol: at 21 days, the media was removed from each well, leaving approximately 100 µL to prevent the cell sheet from drying out. Sterile tweezers were used to gently scrape the outer edge of cell sheet and detach it from the walls of the well (FIG. 1A) and subsequently create a rectangular shape (FIG. 1B) which was folded 2 times along its long axis, hence forming a bundle (FIG. 1C). Four cell sheet bundles were seeded in between the ligament strands of the PCL scaffold (with dorsal surface facing upwards) (FIGS. 1C & D). The fifth cell sheet was placed onto the dorsal surface of the BLB scaffold and therefore was not folded in a bundle. This was achieved by placing the BLB scaffold with dorsal surface facing down onto the detached cell sheet, which was subsequently wrapped around the bone and ligament compartments (FIG. 1E). 2 mL of fresh media was added to a well and scaffolds were incubated at 37° C., 5% CO2 for 4-6 hours to facilitate cell sheet attachment.

Cell Viability

The impact on the cell sheet handling and placement into the scaffold was assessed by measuring cell viability. The scaffolds were seeded with five cell sheets before incubation in media at 37° C., 5% CO2 for six hours. Seeded scaffolds (n=3 per design) and control, flat, non-handled single cell sheets (n=3) were stained with fluorescein diacetate (FDA) and propidium iodide (PI) at 5 µg/mL and 2 µg/mL respectively and incubated for five minutes before visualization using confocal microscopy (Nikon AR1+ Confocal Machine) at 488 nm and 561 nm.

(vii) In Vivo Ectopic Implantation

The regenerative performance of the BLB construct was assessed using a rodent subcutaneous implantation model. In order to recapitulate the healing events occurring in the scaphoid and lunate bone in the clinical setting, a heparinised gelatin-hyaluronic acid gel (HyStem™-HP, Sigma Aldrich) loaded with an osteogenic cue (recombinant Bone Morphogenetic Protein-2, BMP-2, produced in E. coli (Genscript, Hong Kong)) was used for achieving bone formation in the relevant bone compartments.

BLB Scaffold Preparation:

Six different groups were created for the in vivo study; 1) 350 µm BLB scaffold (350 µm Control), 2) 350 µm BLB scaffold with BMP-2 in the bone compartments (350 µm BMP), 3) 350 µm BLB scaffold with BMP-2 in the bone compartments and cell sheets (CS) in the ligament compartment (350 µm BMP-CS), 4) 600 µm BLB scaffold (600 µm Control), 5) 600 µm BLB scaffold with BMP-2 in the bone compartments (600 µm BMP), 6) 600 µm BLB scaffold with BMP-2 in the bone compartments and cell sheets (CS) in the ligament compartment (600 µm BMP-CS).

For the control groups (350 µm Control and 600 µm Control), 25 µL of the heparinised gelatin-hyaluronic-acid hydrogel without BMP-2 was reconstituted as per the manufacturer's instructions for reaching a 1% wt/vol hydrogel composition, and carefully dispensed into each of the bone compartments (FIG. 1F). Scaffolds were incubated at 37° C., 5% CO2 for approximately 45 minutes allowing the gel to set before implantation. The samples containing BMP-2 were prepared using the same method and 25 µg of recombinant human BMP-2 was incorporated into 25 µL of hydrogel while still maintaining 1% hydrogel concentration. To avoid the presence of media in the cell sheet seeded specimens, a 200λ pipette was used to remove any liquid from the bone compartments. This enabled the injection of the BMP-2 loaded hydrogel. The cell sheets were regularly hydrated every 10 minutes by placing a 20 µL, drop of warm media onto the ligament compartment.

Animal Model and Animal Care 8-week old athymic nude CBH-rnu/Arc rats (n=6) from Animal Resource Centre (West Australia) were acclimatised for 7 days before undergoing surgery. All experiments received Griffith University Animal Ethics Approval (Ligament regeneration potential of cell laden polycaprolactone scaffold in immunocompromised rat, approval number DOH/04/15/AEC) and experimentation was adherent to the Australian code for the care and use of animals for scientific purposes.

Ectopic Implantation

Prophylactic antibiotic cover and pre-operative pain relief was provided prior to the surgery using a subcutaneous injection of Keflin® (cephalothin sodium) 20 mg/kg, gentamicin 5 mg/kg and buprenorphine, 0.01-0.05 mg/kg. The animal was placed under ventral recumbency and general anaesthesia (1-3% inhalant to effect (up to 5% for induction) was administered with a Mediquip Isoflurane vaporizer. The surgical field was shaved and disinfected with betadine and six superficial incisions were made. A blunt dissector was used to create pockets in subcutaneous tissue deep enough to fit the scaffolds. Scaffolds were randomly allocated and inserted into a pocket. 4-0 nylon sutures were used to close the wound and betadine was used to disinfect the wound site. Animal revival was assisted using pure oxygen. Postoperatively, multimodal opioid (buprenorphine 0.01-0.05 mg/kg) and an NSAID (carprofen 4-5 mg/kg) were provided in combination subcutaneously to reduce pain. Rats were monitored daily for progression of wound healing for 7 days and then periodically once a week.

Animal Sacrifice and Sample Harvesting

At the 2-week and 8-week time points, the rats (n=3 per time point) were sacrificed the scaffolds were retrieved and immediately fixed in 4% paraformaldehyde for 24 hr before being placed in PBS for subsequent analysis.

(viii) MicroCT

Samples were analysed by microCT (µCT40, SCANCO Medical AG, Brüttisellen, Switzerland) with a voltage of 55 kVp, a current of 120 µA and power of 8 W, an integration time of 300 ms and a voxel size of 20 µm to determine bone mineralisation. 3D images were reconstructed using the microCT software.

(ix) Histology

Hematoxylin & Eosin (H & E)

Samples were decalcified using 5M EDTA at room temperature for 3 weeks prior to dehydration and paraffin embedding using a tissue processor (Shandon™ Excelsior ES, Thermo Scientific, Waltham, USA). 5 µm longitudinal slices of the constructs were sectioned and collected on polylysine-coated slides. These samples were deparaffinised with xylene before rehydration with decreasing concentrations of ethanol. Sections were stained with H&E and scanned with an Aperio AT2 Console (Leica Biosystems Imaging Inc., USA).

Histomorphometry was conducted using the Osteomeasure Histomorphometry suite. The surface area occupied by bone mineralisation, early stages of mineralisation and fibre alignment in the ligament compartment were measured in order to quantify the performance of the different scaffold designs.

(x) Statistics

Unpaired, parametric, two-tailed T tests with Welch's correction was conducted for tensile tests, compressive tests, scaffold porosity, DNA and collagen quantification results. One-way ANOVA was used for determining statistical significance in cell viability as more than 2 means were compared. The data from the in vivo study (µCt and histomorphometry) were analysed using the General Estimation Equation using IBM SPSS Statistics for Windows version 21.0 (IBM Corporation 2012©, Armonk, N.Y., USA) with individual animals as the clustering variable. Time and group were used as explanatory variables along with all two-way interactions. A backward elimination procedure was used for arriving at the most parsimonious model. A $p<0.05$ was considered to represent statistically significant differences.

Results (i) Scaffold Morphology

Figure 2:
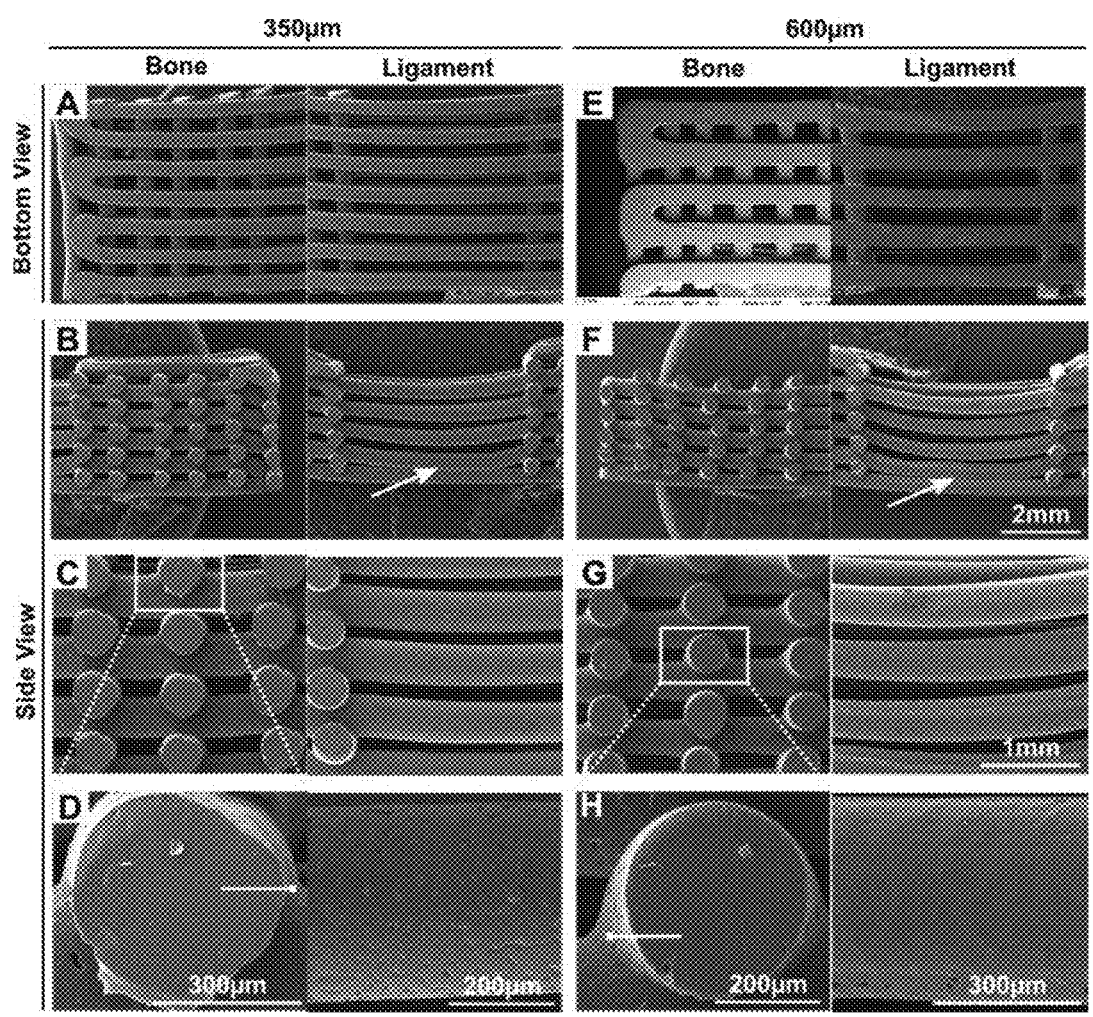
FIG. 2 provides SEM images of 350 µm and 600 µm porosity BLB constructs. of 350 µm and 600 µm porosity BLB constructs. Sagging of PCL fibres is indicated by the white arrows. PCL fibre fusion between adjacent layers is indicated by the square arrows. A) Bottom view of 350 µm bone compartment at 40× magnification. B-D) Cross-sectional view of 350 µm bone compartments at 40×, 100× and 500× magnification illustrating good fusion between PCL strands of each layer. E) Bottom view of 600 µm bone compartment at 40× magnification. F-H) Cross-sectional view of 600 µm ligament compartments at 40×, 100× and 500× magnification.

The morphology of the scaffolds was investigated by SEM and this revealed the production of two architecturally highly distinct components within the construct; the two extremities (bone compartments) of the BLB-scaffold consisted of the typical alternating 0/90 angle polymeric struts layer (FIGS. 2A and E), whereas the ligament compartment, as per our printing design, was composed of aligned and superimposed struts creating macroscopic grooves (FIGS. 2B and F). While additive manufacturing theoretically allows the creation of various shapes and dimensions, it is challenging for the internal porous structure or strut layout to be varied throughout the scaffold printing. In order to achieve this dual architecture, an in-house g-code production software was used to permit manual modification of the internal layout of the scaffold and resulted in the creation of aligned struts. Importantly, the struts composing the ligament compartment are completely integrated within the bone compartments hence ensuring a mechanically strong cohesion, while maintaining a porous interface.

In this sense, the BLB-scaffold is a biphasic scaffold, having two architecturally different portions, but manufactured in a continuous manner similarly to a monolithic 3D printed construct. SEM imaging showed that the strut diameter was 420 µm±24.49 µm (n=5) and that there was adequate fusion between layers for both of the 350 µm and 600 µm designs (FIGS. 2C and H, square arrows), thereby ensuring a strong interrelation between the layers. The mPCL struts in the ligament compartment were homogenous in width, although some sagging was observed (FIGS. 2B and F, white arrows). This can be explained by the fact that the mPCL was extruded well above its melting point and hence was in a semi-molten state when deposited. Furthermore, there was a lack of adjacent support over the length of the ligament compartment hence resulting in filament sagging. While this was an inherent limitation of the design, this event was limited to a few struts and did not compromise the function of the scaffold.

Figure 3:
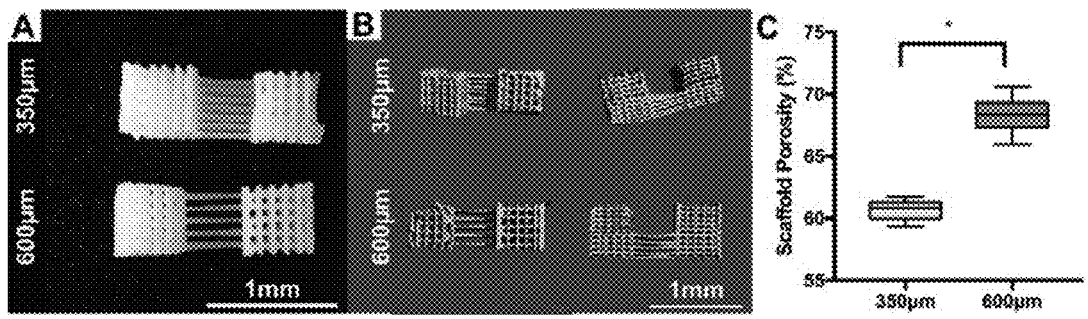
FIG. 3 shows 350 µm and 600 µm porosity BLB constructs. A) 3D-printed PCL scaffolds. B) 3D-reconstructions of microCT scans. C) Scaffold porosity of 350 µm and 600 µm porosity scaffolds.

MicroCT analysis of the scaffolds enabled the determination of the BLB-scaffold porosity (FIG. 3). While the 600 μm design resulted in a 70% porosity, the 350 μm design displayed a porosity around 60%. This result was expected as the 350 μm design had more material per unit volume printed due to a smaller inter-fibre interdistance.

(ii) Mechanical Properties

Figure 4:
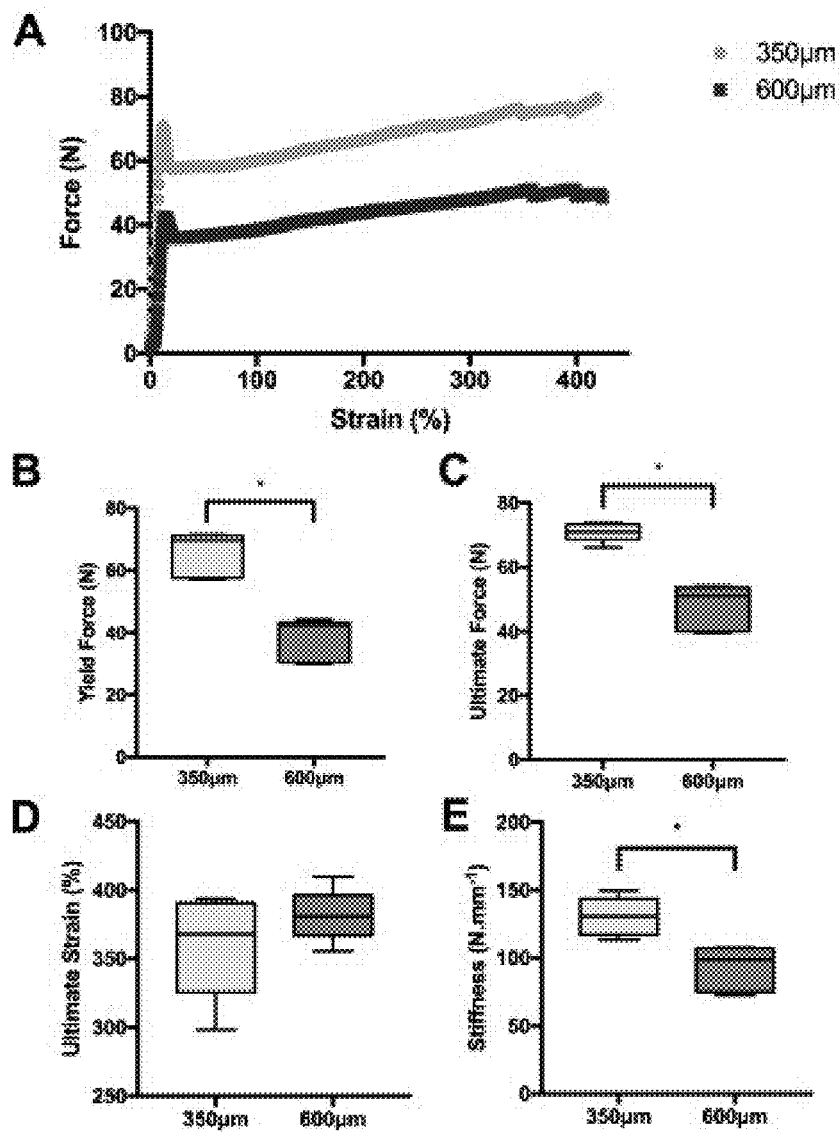
FIG. 4 shows tensile test results of ligament compartment. Tensile testing results at elongation rate of 20 mm/min. A) Force Vs Strain displacement curves of 350 µm and 600 µm scaffolds. B) Yield force of 350 µm and 600 µm scaffolds. C) Ultimate force of 350 µm and 600 µm scaffolds. D) Ultimate strain of 350 µm and 600 µm scaffolds. E) Stiffness of 350 µm and 600 µm scaffolds.

The mechanical properties of the construct were assessed in both tension and compression, under quasi-static and cyclic loading. The 3D-printed scaffold displayed a typical force-strain curve of polymeric material composed of an initial linear region followed by a yield point and a plastic deformation region (FIG. 4A). As expected, the 350 μm BLB-scaffold was the strongest construct with a yield force around 65N and an ultimate force of 70N, whereas the 600 μm displayed a yield and ultimate force of 40N and 50N respectively. Similarly, the less porous 350 μm BLB-scaffold was significantly stiffer than the 600 μm BLB scaffold with a stiffness of 130 N·mm-1 and 90 N·mm-1 respectively. Table 1 lists the mechanical parameters measured for the quasi-static tensile test and compares them to the properties of the human native tissue. It is evident that the ultimate force of both constructs are substantially lower than the anatomic SLIL complex. However the physiological load withstood by the ligament is in the range of 20N which is still in the elastic range of the BLB-scaffold.

TABLE 1

Tensile testing results of the 350 μm/600 μm scaffold as compared to the native dorsal SLIL.

|  | 350 μm scaffold (n = 5) | 600 μm scaffold (n = 5) | Native Dorsal Scapholunate ligament |
|---|---|---|---|
| Yield Force (N) | 65.5 ± 6.47 | 38.01 ± 6.25 |  |
| Ultimate Force (N) | 71 ± 2.66 | 47.7 ± 6.40 | 185.3 ± 87N (21) Normal physiological load on SLIL during cyclic motion is 20N (22) |
| Ultimate Strain (%) | 360.1 ± 34.13 | 381.5 ± 17.25 |  |
| Linear Stiffness (N · mm$^{-1}$) | 130.6 ± 12.54 | 92.48 ± 14.93 | 162 ± 86.4 (21) |

Compressive Testing of Bone Compartment

Figure 5:
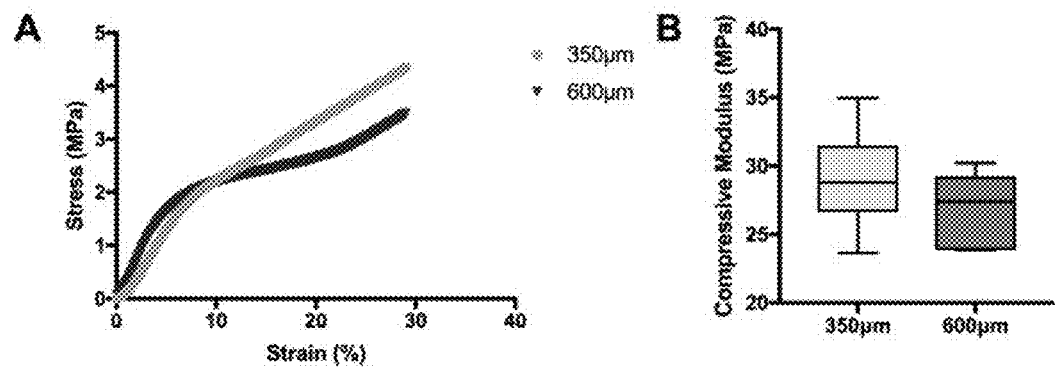
FIG. 5 shows graphs depicting compressive behaviour of the bone compartment. A) Representative stress-Strain curves of 350 µm and 600 µm scaffolds, B) Compressive modulus of 350 µm and 600 µm porosity bone compartments.

The mechanical compressive behaviour of the bone compartment was also investigated (FIG. 5) and this revealed that despite changes in the scaffold internal microstructure, there was no significant difference between the compressive modulus of the two designs (350 μm: 29.03±3.35 MPa; 600 μm: 26.94±2.37 MPa (p>0.05)).

(iii) Cyclic Testing

Figure 6:
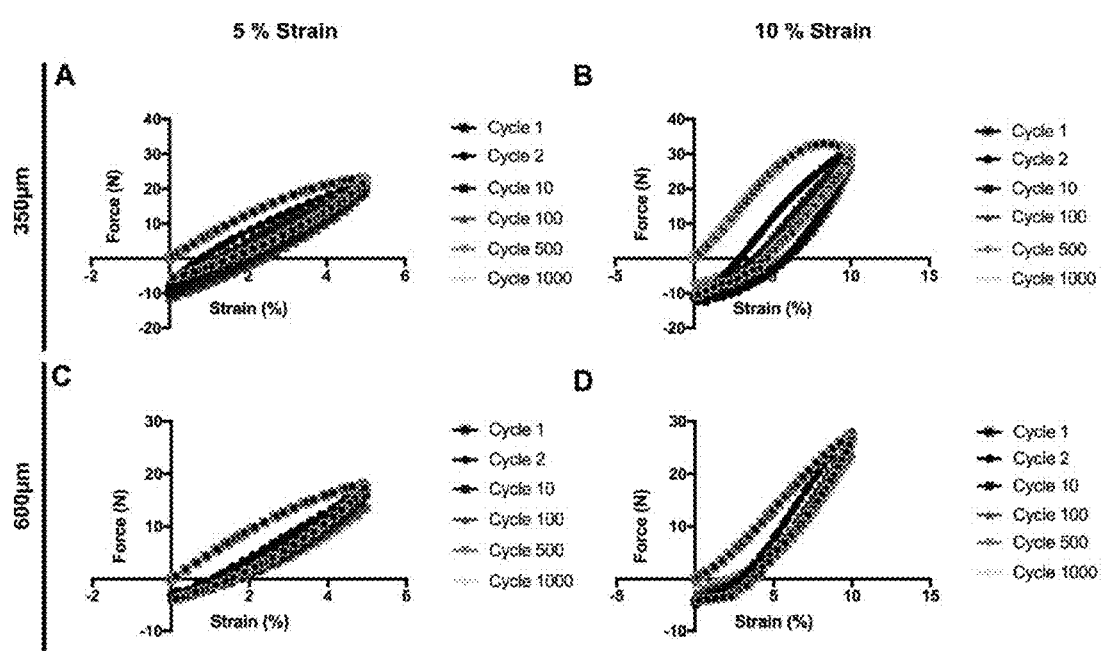
FIG. 6 shows cyclic testing hysteresis loops for scaffold designs at 5% and 10% strain.
Figure 7:
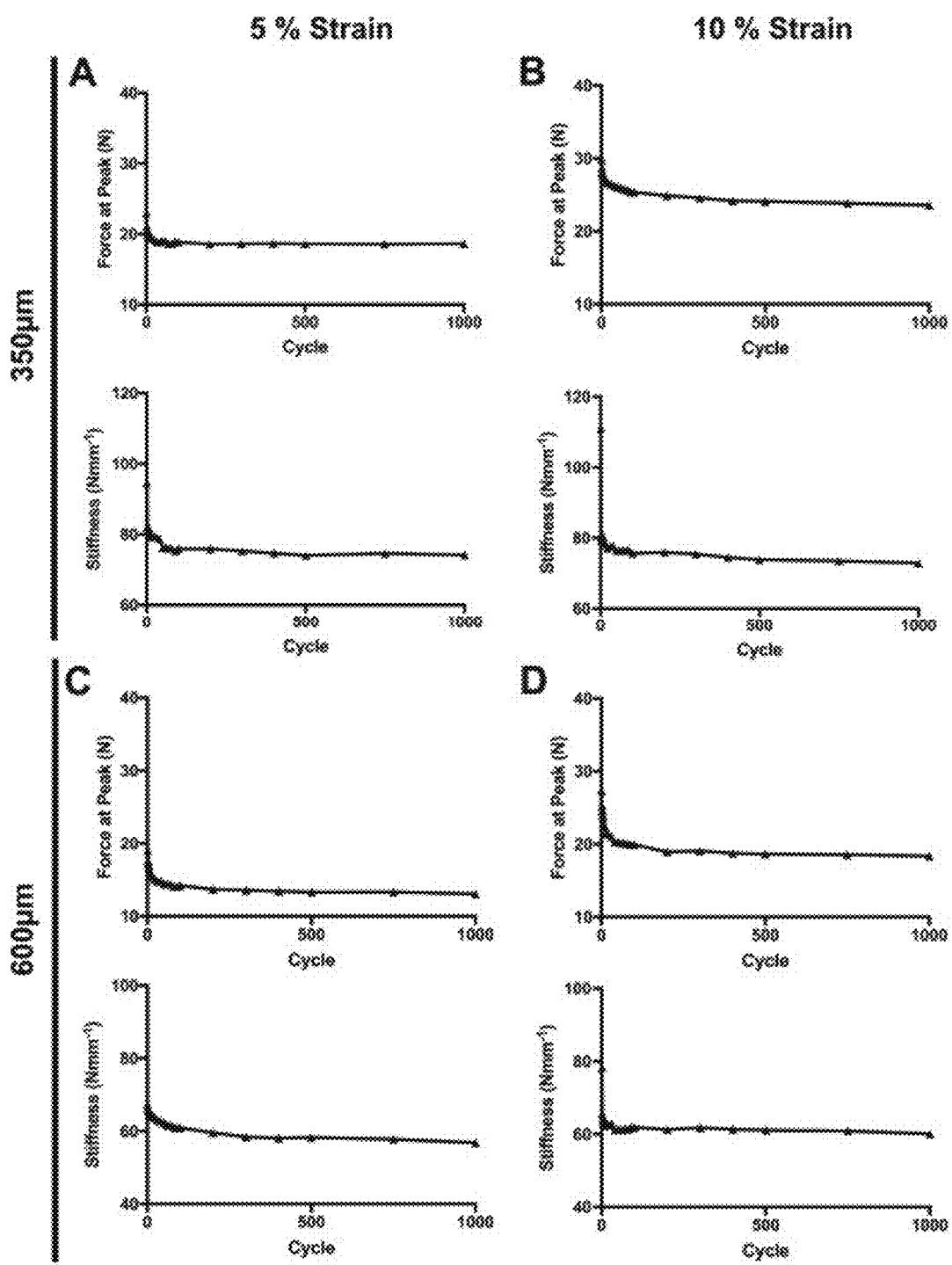
FIG. 7 provides graphs indicative of construct stiffness. Changes in ultimate force over 1000 cycles are shown for each scaffold design. Curves are representative of the 5 samples tested.

In order to further assess the suitability of the BLB scaffold for functional regeneration of the scapholunate ligament, the mechanical behaviour was investigated under dynamic conditions. The testing parameters, 5 and 10% strain at 0.5 Hz, were selected as they represented, to some extent, the physiological extension that the native tissue withstands during normal motion. For both designs, 350 μm and 600 μm, the scaffolds displayed a high level of recovery as shown in FIG. 6 by the superimposition of the deformation hysteresis. No accumulation of plastic deformation was noted over the 1000 cycles of the experiment. Interestingly, the scaffolds withstood some level of compression upon returning to zero strain. This indicates that the polymer did not fully recover from the stretching and therefore the scaffold withstood some level of compressive forces. Notably, the level of compression did not change for a given design regardless of the stain applied (5 or 10%), however the stiffer construct (350 μm) experienced a higher level of compression. The evolution of the force at peak was plotted against cycle number and this demonstrated that the force at peak sharply decreased after the first cycle and remained relatively constant thereafter, indicating that strain-induced relaxation occurred in the BLB construct (FIG. 7). Similarly, the construct stiffness was evaluated and this revealed a differential behaviour between the 350 μm and 600 μm design (FIG. 7). Indeed, the 350 μm design, which is the stiffer construct, could better retain of its stiffness as the percentage decrease in this parameter was less at both 5% and 10% strain (Table 2). However, the less rigid construct (600 μm) displayed a decrease in the stiffness of about 20-30% for both strains. This indicates that from a biomechanical point of view, the 350 μm is potentially a better candidate for SLIL reconstruction. It is also worth noting that despite the softening of the constructs, the force at peak remained in the range of the physiological loading experienced by the native ligament.

TABLE 2

Percentage decrease between cycles 1 and 1000 in force at peak and stiffness of each construct at 5% and 10% strain

|  | 5% Strain Percentage decrease | | 10% Strain Percentage decrease | |
|---|---|---|---|---|
|  | Force at Peak | Stiffness | Force at Peak | Stiffness |
| 350 μm (n = 5) | 18 ± 1% | 15 ± 1%* | 20 ± 2%* | 24 ± 3% |
| 600 μm (n = 5) | 24 ± 3% | 20 ± 1%* | 33 ± 3%* | 31 ± 3% |

(*denotes statistical significance at p < 0.05 between designs).

(iv) Cell Sheet Characterisation

Figure 8:
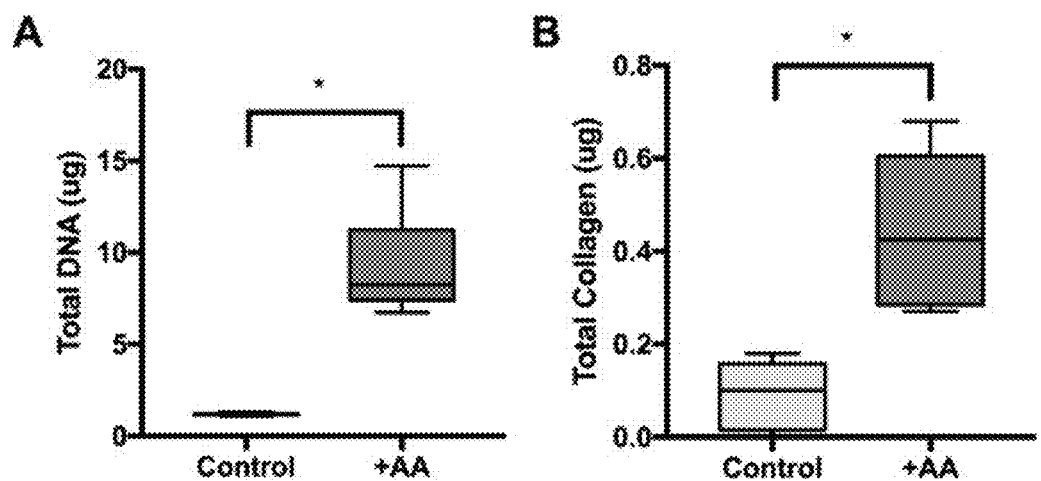
FIG. 8 provides DNA and Collagen quantification results. DNA and collagen quantification of cell sheets. +AA groups demonstrated significantly greater cellular proliferation and collagen synthesis when compared to the controls (−AA). Bars show statistical significance ($p<0.05$).
Figure 9:
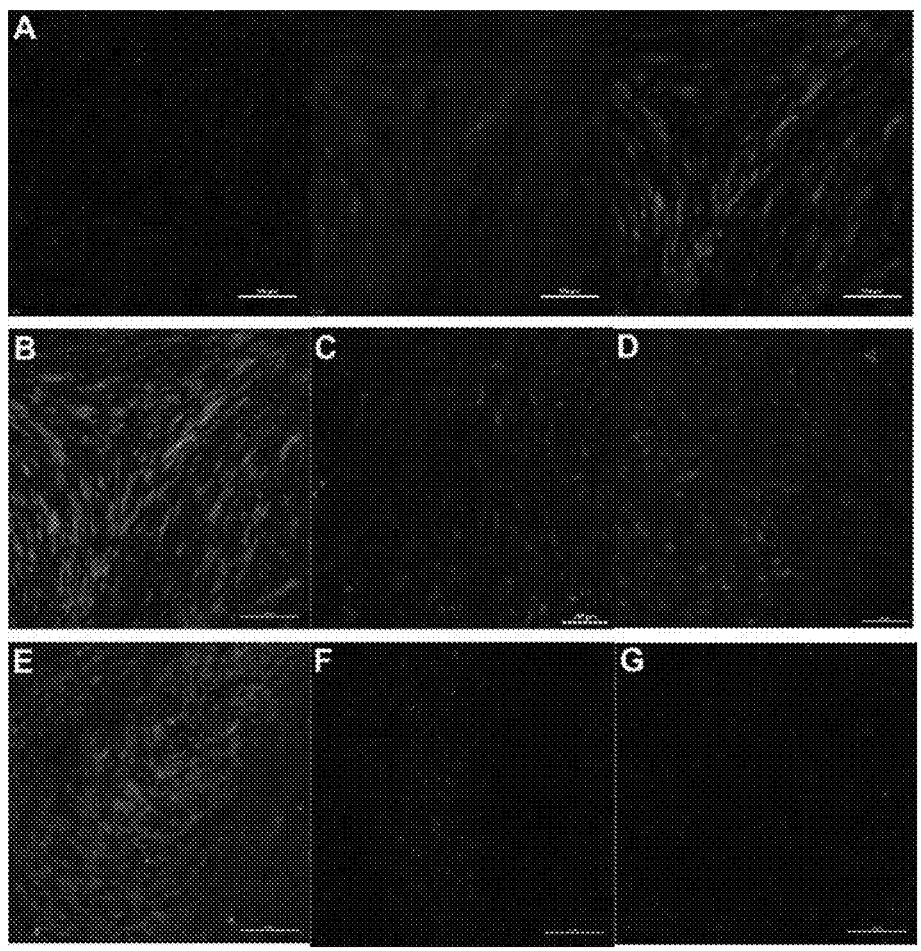
FIG. 9 shows the results of immunofluorescence staining for ECM proteins. A—Collagen Ia (green)/III (red) staining; B—Tenascin C; C—Elastin; D—Aggrecan; E—Mouse isotypic control; F—Rabbit isotypic control; G—anti-mouse secondary antibody only; H—anti-rabbit secondary antibody only

One pertinent advantage of utilising cell sheet technology is that the extended cell culture duration facilitates maturation and increased deposition of the cell's own ECM prior to implantation. As such, the cell sheet utilised in the current study were characterised by measuring DNA content as an indicator of relative cell number and collagen deposition (FIG. 8). Total DNA content of and collagen synthesis by the human bmMSC cell sheets cultured in ascorbic acid supplemented medium were significantly higher than that of control cells cultured in expansion media. The low amount of DNA detected in the control samples can be attributed to decreased proliferation and increased cell death over the 21-day culture period with DNA being discarded with each media change. Immunofluorescence of Collagen 1a, Collagen III, Elastin, Tenascin C and Aggrecan showed dense and homogenous distribution of extracellular matrix with a fibular structure in +AA groups (FIG. 9). This was not seen in the control group cultured without ascorbic acid. Isotype and secondary antibody controls only demonstrated minimal background.

(v) Assembly of Cellularised Construct

Figure 10:
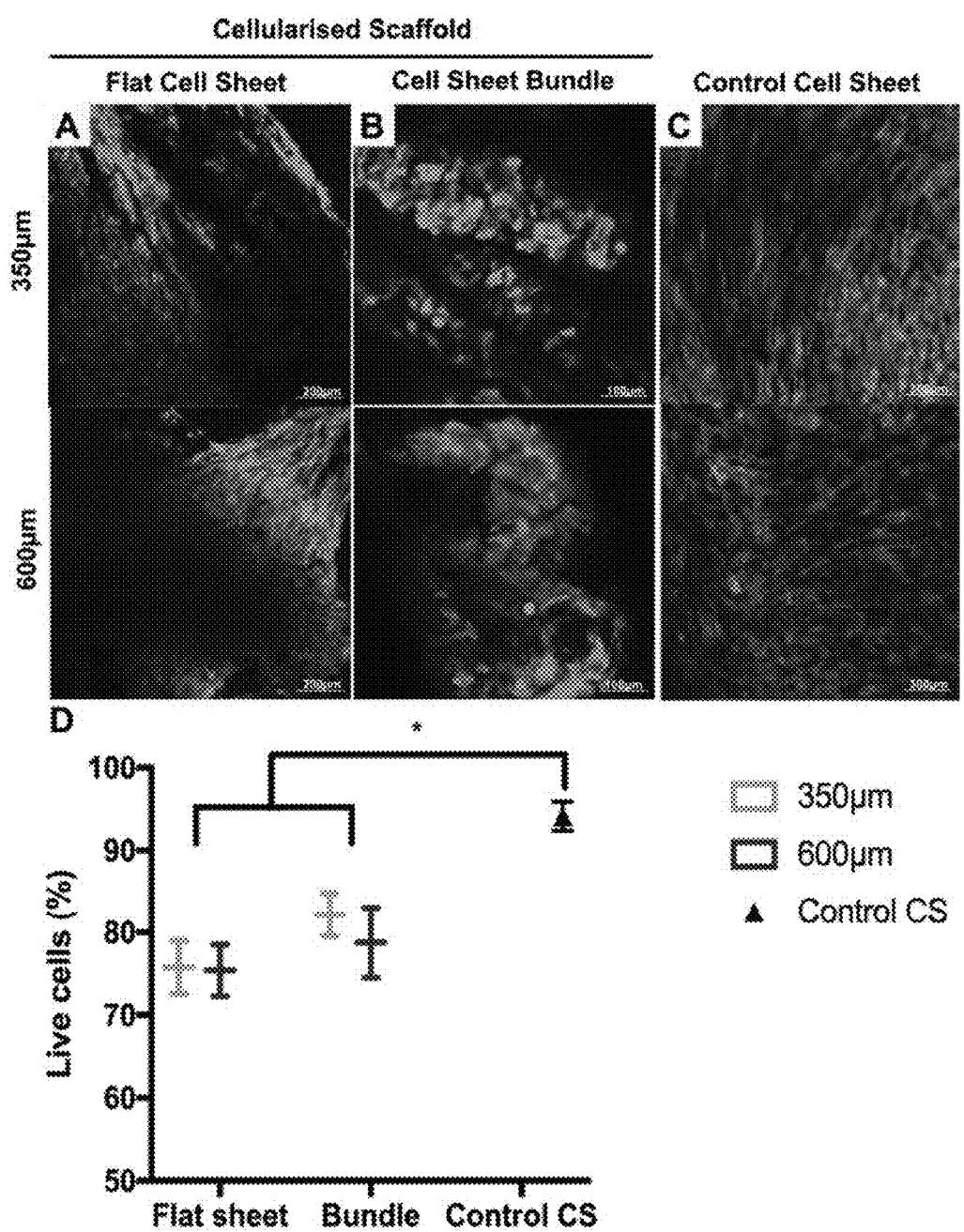
FIG. 10 shows the results of a cell viability analysis on seeded and non-seeded cell sheets with FDA (green, live cells) and PI (red, dead cells). A) Representative images of flat cell sheets wrapped around dorsal surface of BLB scaffold, B) cell sheet bundle placed in between PCL fibres of ligament compartment and C) non-harvested cell sheets (control). D) Percentage of live cells in flat sheet and bundles of 350 µm and 600 µm scaffold.

Live dead assay was conducted to evaluate the impact of the assembly method, utilising mechanical harvesting and rolling of the cell sheets, on cell viability (FIG. 10).

FIGS. 10A-C presents the confocal laser microscopy images indicating that most of the cells were alive (green staining). While the non-harvested control cell sheets had the highest cell viability with over 90% live cells, this only decreased slightly to approximately 80% live cells in the seeded cell sheets of both designs. There was no statistically significant difference in cell viability between the bundled cell sheets and the flat cell sheet placed on the dorsal surface of the ligament compartment, and this was observed regardless of the design. There was a statistically significant difference in cell viability between the cell sheets in the constructs and the control cell sheets (p<0.05) (FIG. 10D).

(vi) SEM (Cellularised Construct)

Figure 11:
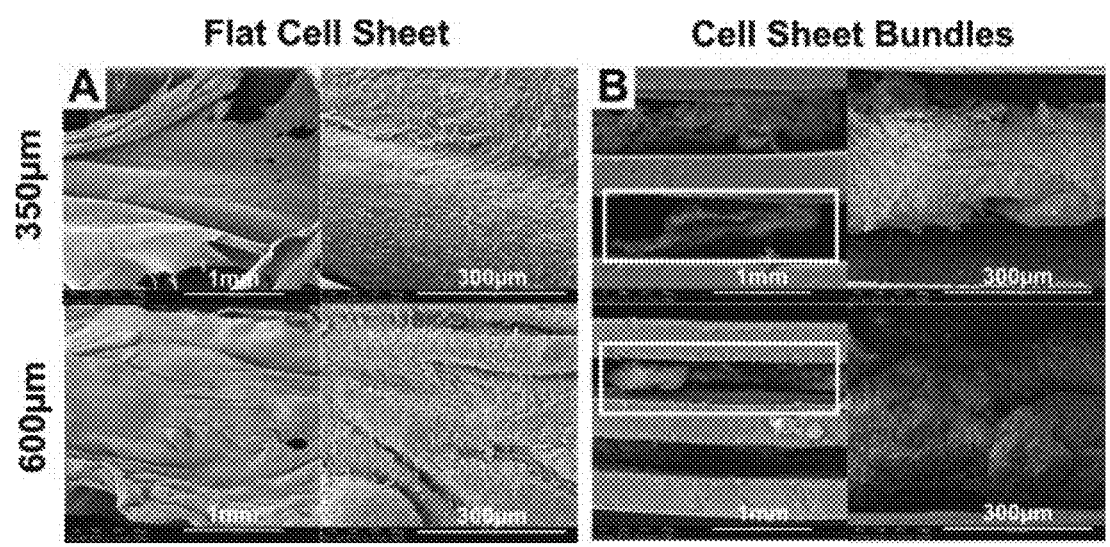
FIG. 11 provides SEM images of a cellularised BLB construct. SEM of cellularised BLB construct. A) 350 µm and 600 µm pore size scaffolds with flat cell sheet at 100× and 500× magnification. Dense extracellular matrix fibres are visible. B) 350 µm and 600 µm pore size scaffolds with cell sheet bundles at 100× and 500× magnification.

SEM visualisation of the cellularised scaffolds illustrated extensive ECM matrix in the cell sheets (FIG. 11).

(vii) Ectopic Implantation

The regenerative performance of the BLB construct was assessed ectopically in athymic rats using an ectopic model. The cellularised constructs were implanted six hours post-assembly and the bone formation along with soft tissue regeneration were measured at 2 and 8 weeks post-implantation.

Bone Mineralisation

Figure 12:
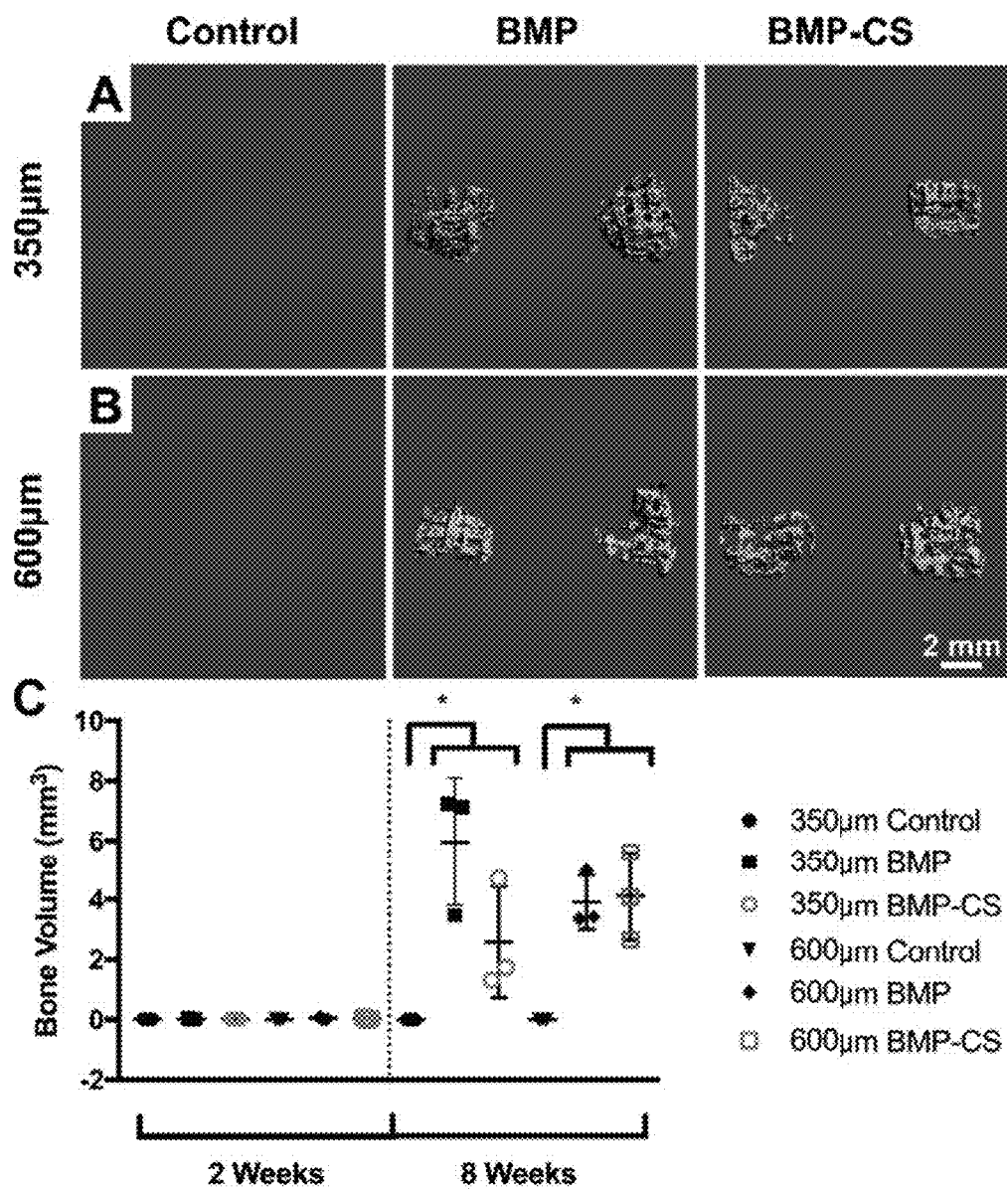
FIG. 12 shows the results of a MicroCT analysis of bone mineralisation. A-B) 3D reconstructions of bone mineralisation in 350 µm and 600 µm porosity scaffolds. C) Bone volume in 350 nm and 600 µm porosity scaffolds at 2 weeks and 8 weeks.

The evaluation of bone formation within the construct was performed by microcomputed tomography. This revealed that while no bone was detected at 2 weeks post-implantation, significant amount of mineralised tissue was observed at 8 weeks post implantation (FIG. 12). As expected, the new bone followed the pattern of the 3D printed structure, forming in the space surrounding the polymeric filament (FIG. 12A) and more importantly was restricted to the bone compartment. This demonstrated that the method of BMP-2 delivery did not result in ossification within the ligament compartment, hence indicating that a high level of compartmentalisation was achieved despite the presence of a porous interface. The quantification of bone formation at 8-week post implantation revealed that there were no statistically significant differences between the two designs. Similarly the presence of the cell sheets did not affect the degree of mineralisation (FIG. 12C).

(viii) Histology

Figure 13:
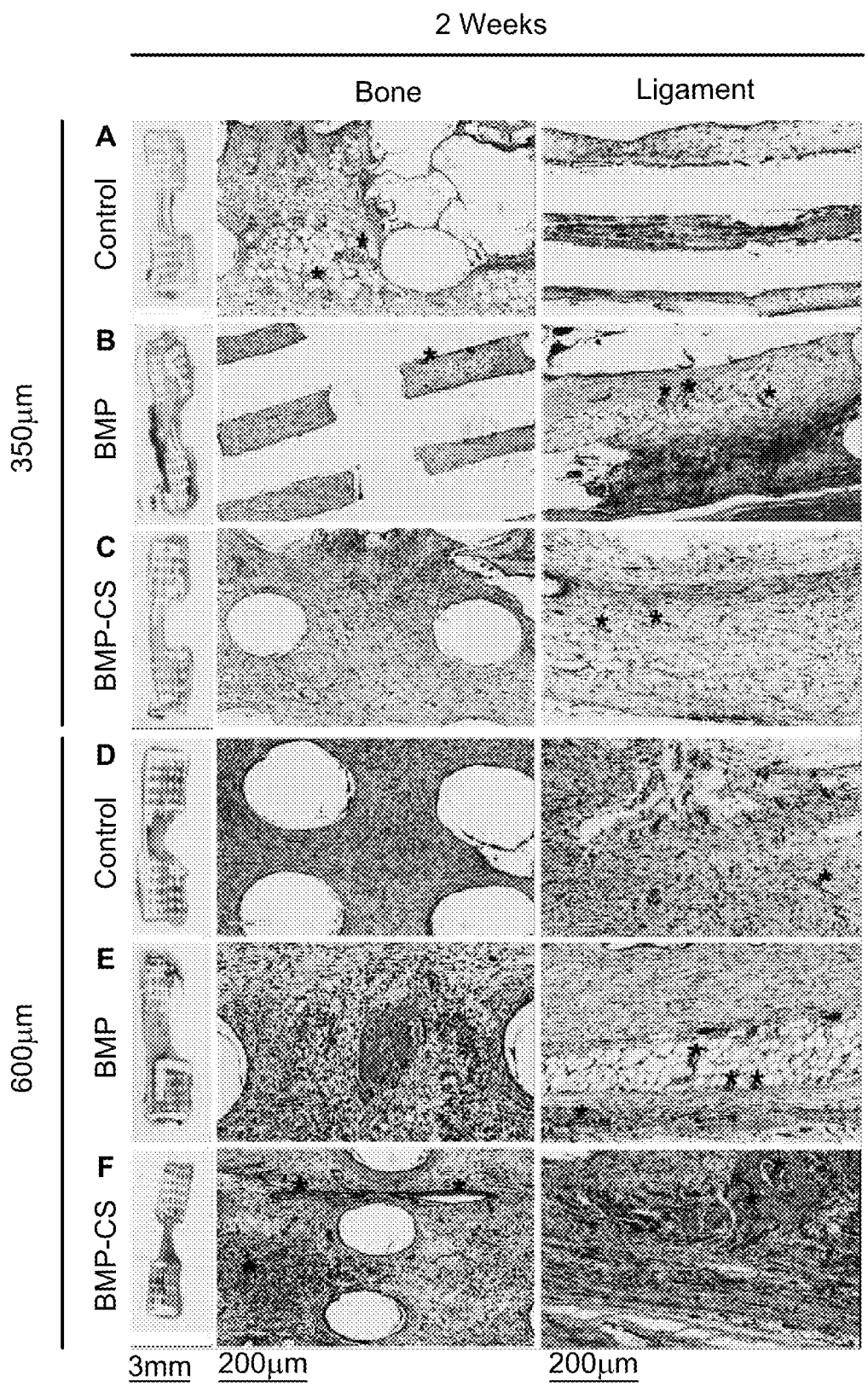
FIG. 13 shows histological images of Haemotoxylin and Eosin (H&E) stained bone-ligament-bone constructs implanted for 2 weeks. Some sections of the ligament compartment do not picture PCL struts as these sections were taken in between struts. The stars mark the presence of blood vessels.

The histology showed that both compartments had high amounts of tissue infiltration as early as 2 weeks post implantation, as expected for this type of scaffold and pore size. The scaffold compartmentalisation was also confirmed as no traces of bone formation were observed in the ligament compartment at the later time point (FIG. 13).

Bone Compartment

There was an absence of bone formation at 2 weeks post-implantation although some early signs of mineralisation were identified in some samples loaded with BMP-2. Indeed, dense cellular regions enriched in collagen matrix were observed (FIG. 13) characteristic of early stages of mineralisation. Fatty marrow was also dispersed in the bone compartments. At 8 weeks (FIG. 14), there was some bone formation localised to the bone compartments in the samples treated with BMP-2 which corroborated the microCT findings.

Figure 15:
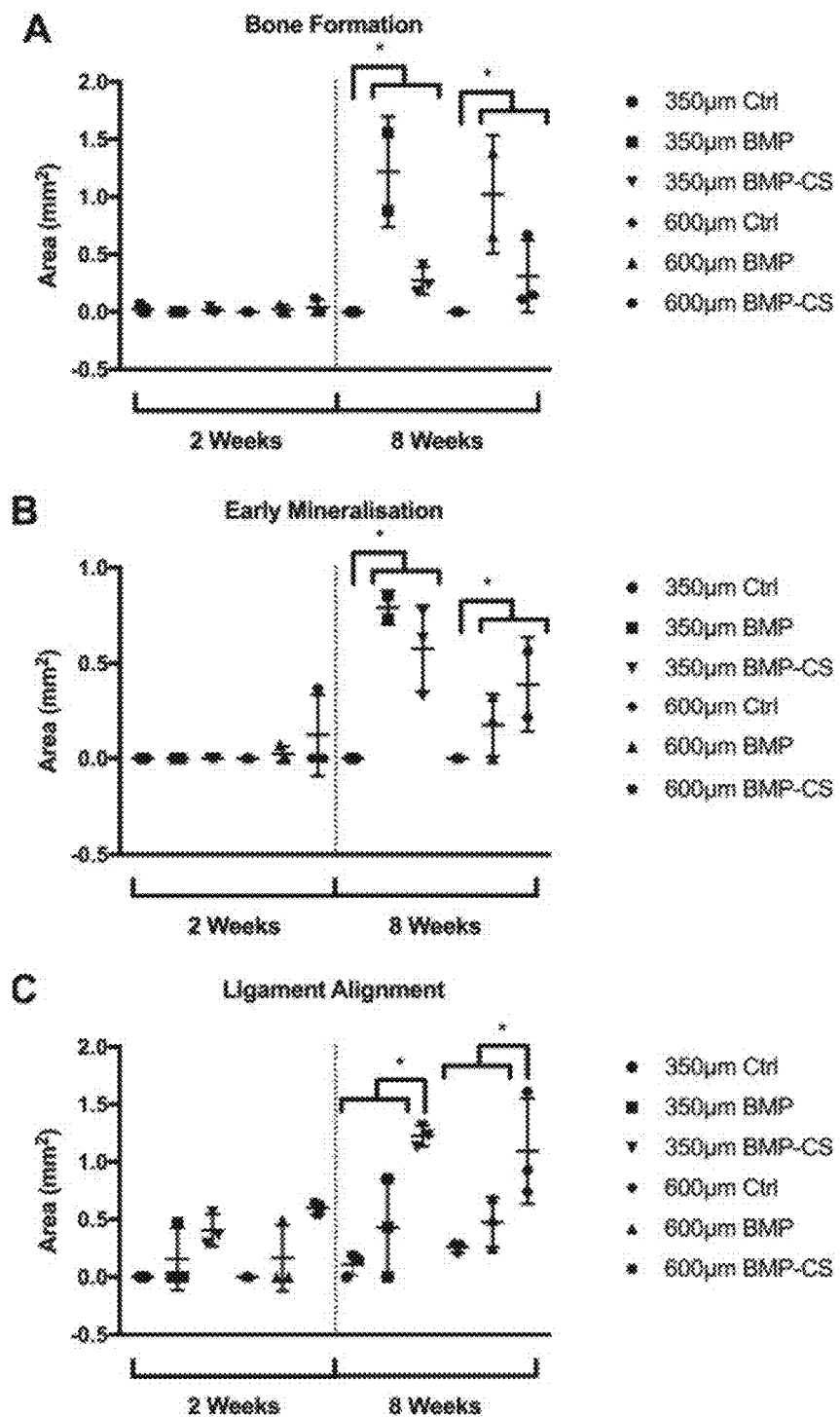
FIG. 15 shows the results of a histomorphometry analysis of bone formation, early mineralisation and ligament alignment in the samples at 2 weeks and 8 weeks. Bars show statistical differences (p<0.05).

However, there was no statistically significant difference in bone formation between BMP and BMP-CS groups or between 350 μm and 600 μm designs at this later time point (FIG. 15).

Ligament Compartment

Figure 14:
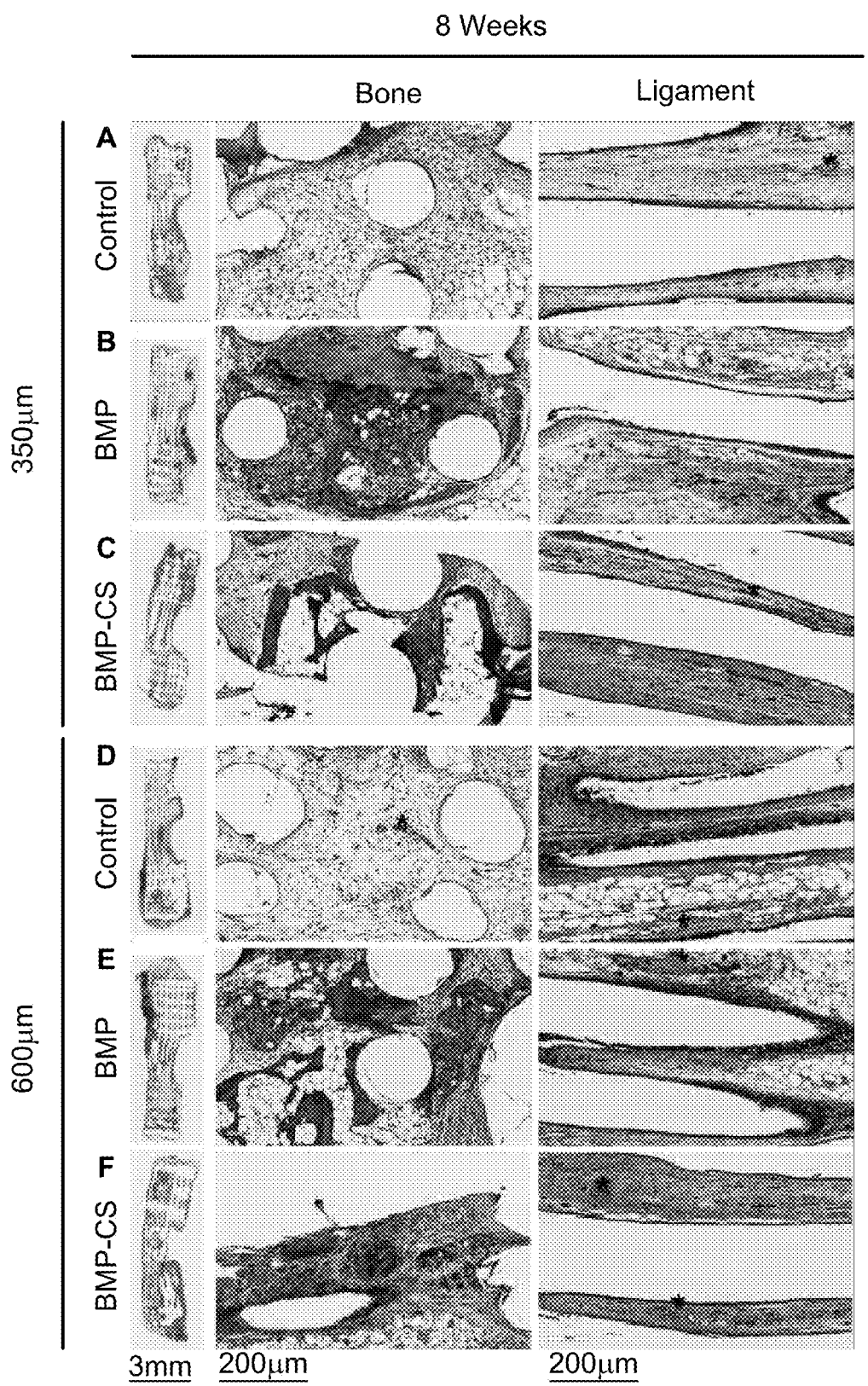
FIG. 14 shows histological images of H&E stained bone-ligament-bone constructs implanted for 8 weeks. The stars marks the presence of blood vessels.
Figure 16:
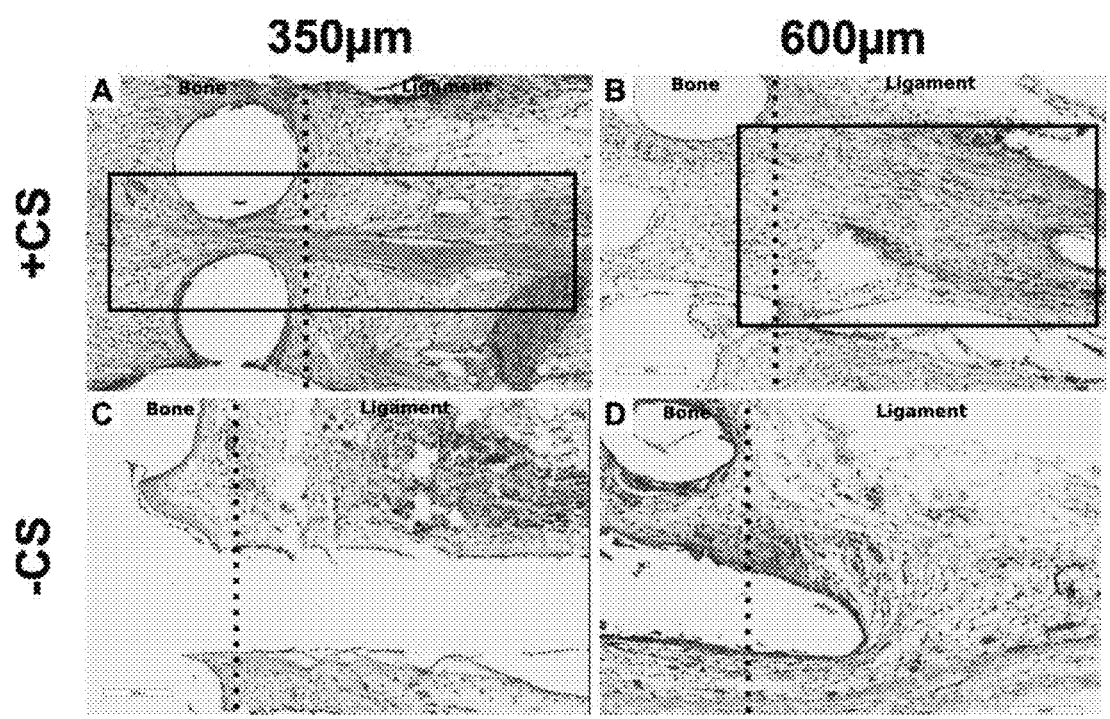
FIG. 16 shows histological images from H&E staining of the bone-ligament interphase in samples implanted for 8 weeks. The dashed line represent the interface between the bone and ligament compartment.

The ligament compartment was vascularised rapidly and remained vascularised as indicated by the presence of vessel structures with erythrocytes in week 2 and 8 H&E sections (FIGS. 13 and 14, indicated by *). At both time points, the presence of the cell sheets had a significant impact on the morphology of the regenerated tissue which was denser, enriched in collagen and more structured as shown in FIGS. 13 and 14. This was best reflected by the presence of aligned collagenic fibres in the midsections of the ligament compartment of the cellularised constructs. This highlighted the fibre-guiding properties of the scaffold architecture during tissue regeneration. Overall, there were no significant differences in the degree of ligament alignment between all groups at 2 weeks (FIG. 15). However, a significantly higher degree of ligament alignment was observed in the 350 and 600 μm BMP-CS groups at 8 weeks, when compared to the other groups, although there was no significant difference between the two designs containing cell sheets (FIG. 15). This indicated that the fibre guidance capacity of the scaffold and the presence of cell sheets worked synergistically for orientating the newly formed ligament. In some instances, the aligned fibres inserted into each bone compartment, thereby forming a continuous bone-ligament-like interphase (FIG. 16).

(ix) Physical Properties of Scaffold Constructs

Figure 17:
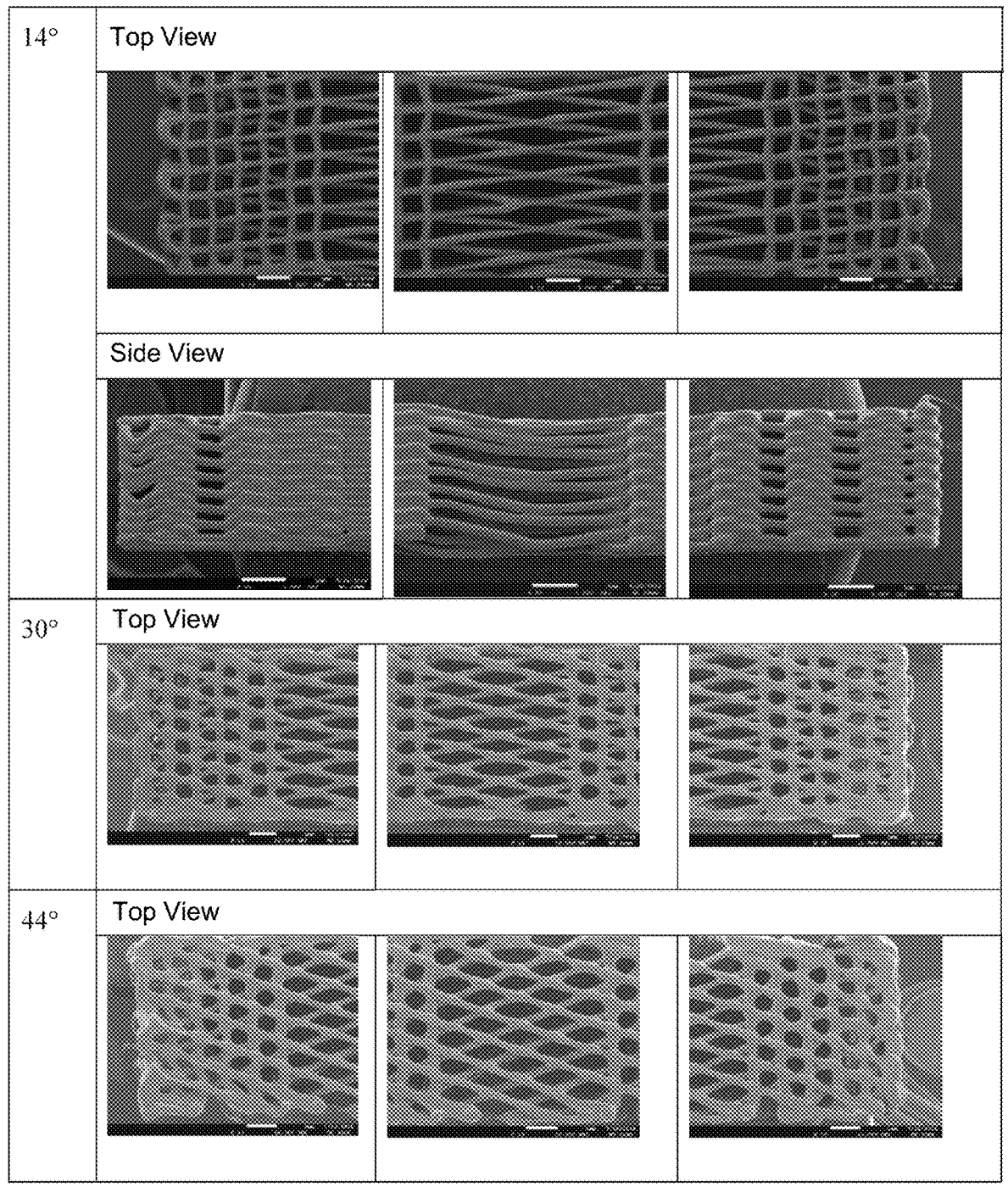
FIG. 17 shows SEM images of scaffold constructs comprising individual layers disposed at different angles relative to one another.
Figure 18:
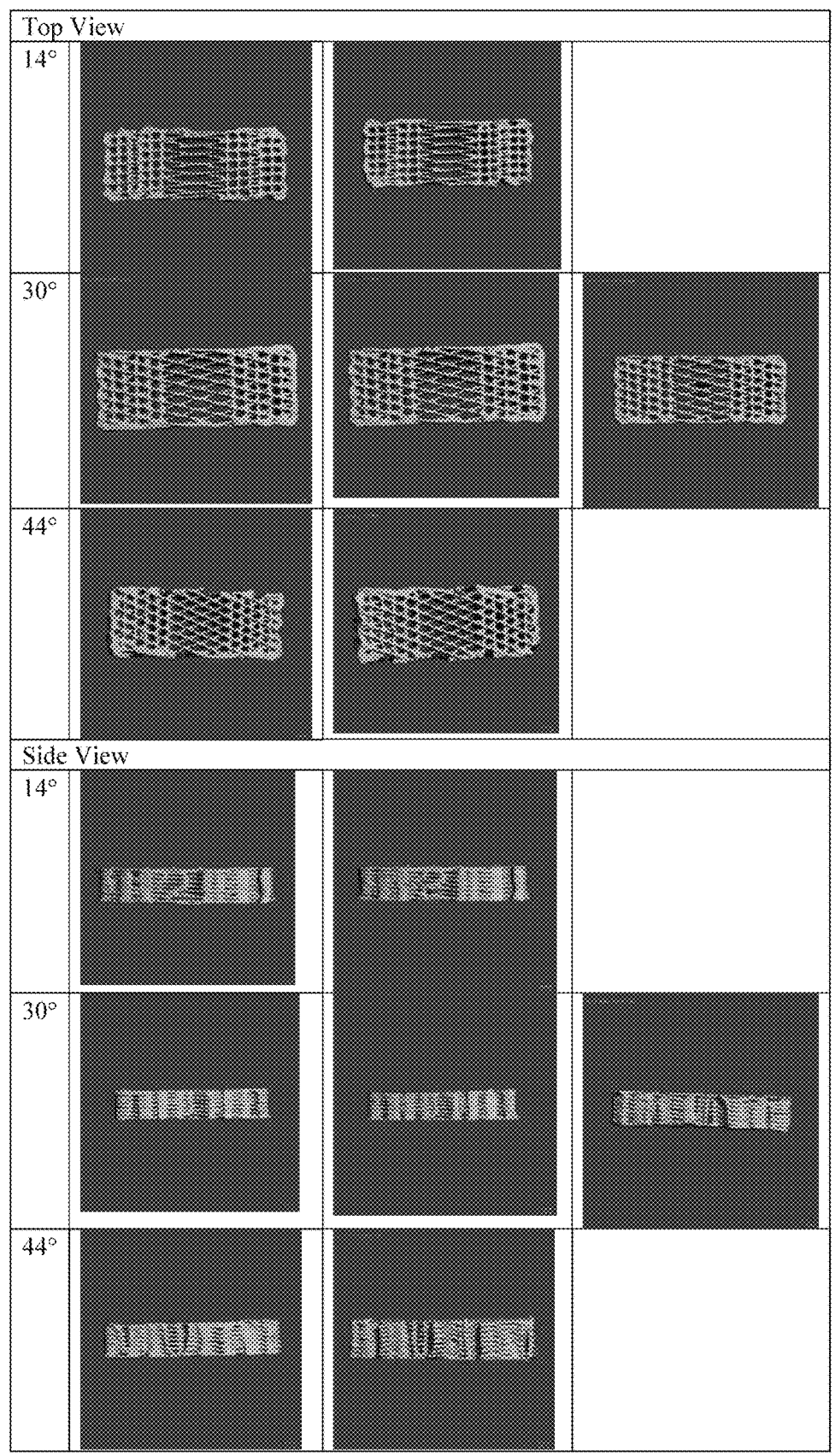
FIG. 18 shows MicroCT images of scaffold constructs comprising individual layers disposed at different angles relative to one another.
Figure 19:
FIG. 19 provides a graph indicating the degree of stiffness observed in various scaffold constructs comprising individual layers disposed at different angles relative to one another.
Figure 20:
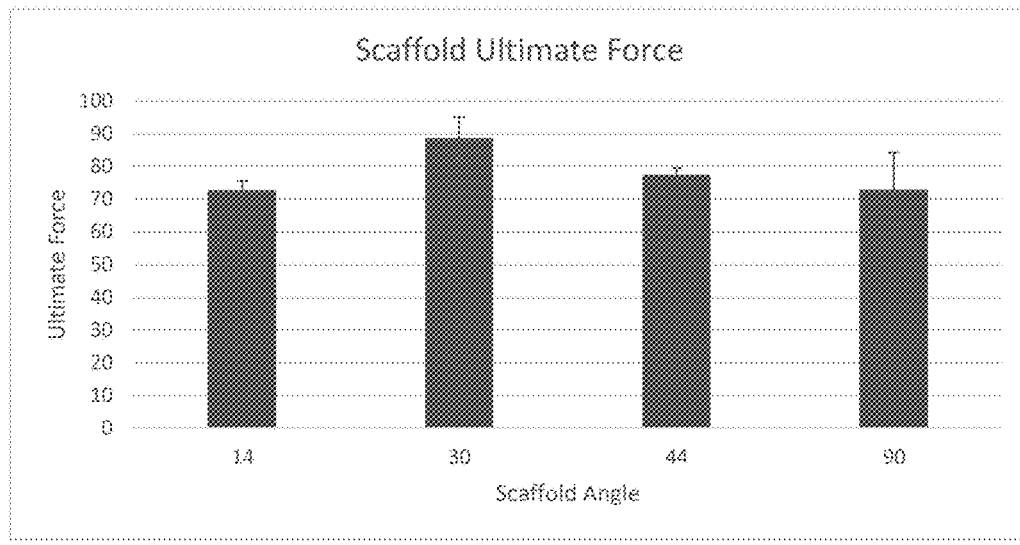
FIG. 20 provides a graph indicating the ultimate force of various scaffold constructs comprising individual layers disposed at different angles relative to one another.
Figure 21:
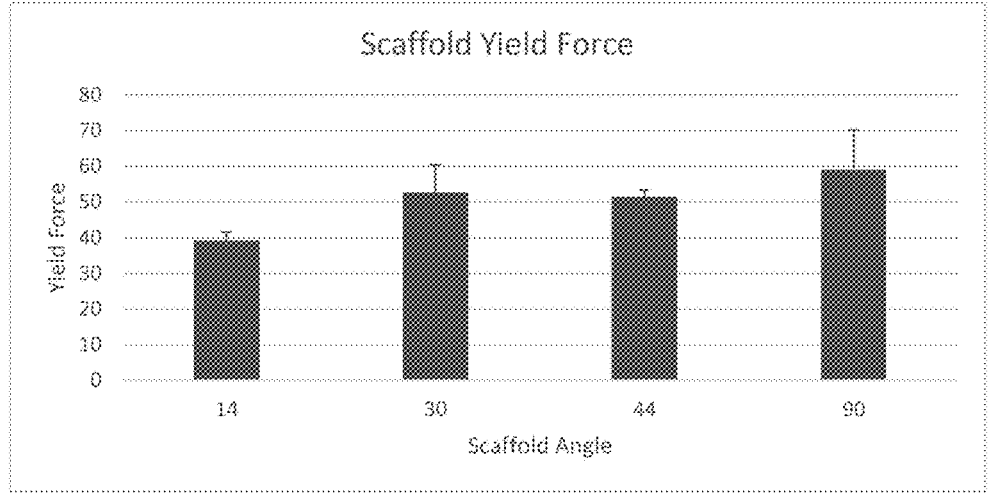
FIG. 21 provides a graph indicating the yield force of various scaffold constructs comprising individual layers disposed at different angles relative to one another.

Images of 3D printed scaffolds comprising individual layers disposed at different angles relative to one another are shown in FIGS. 17 and 18. Various testing was conducted including porosity (Table 3) mechanical testing (quasi-static, tensile):

stiffness (Table 4, FIG. 19)

ultimate force (Table 5, FIG. 20)

yield force (Table 6, FIG. 21)

TABLE 4

| | Stiffness | | | |
|---|---|---|---|---|
| | 14° | 30° | 44° | 90° |
| 1 | 114.57 | 77.62 | 100.38 | 98.704 |
| 2 | 110.21 | 127.93 | 97.145 | 106.06 |
| 3 | 70.604 | 121.72 | 99.873 | 97.429 |
| 4 | 99.406 | 106.21 | 102.99 | 102.1 |
| 5 | | 132.41 | 103.24 | 107.08 |
| Average | 98.6975 | 113.178 | 100.7256 | 102.2746 |
| Standard Dev | 19.78400555 | 22.21137929 | 2.505832057 | 4.29187113 |

TABLE 5

| | Ultimate Force | | | |
|---|---|---|---|---|
| | 14° | 30° | 44° | 90° |
| 1 | 71.2043 | 81.5835 | 77.9534 | 63.06466 |
| 2 | 73.86579 | 82.69795 | 78.3214 | 87.20993 |
| 3 | 76.02313 | 89.31603 | 79.9666 | 60.215 |
| 4 | 70.02915 | 95.54753 | 74.47792 | 79.84805 |
| 5 | | 94.10344 | 76.36821 | 74.13217 |
| Average | 72.7805925 | 88.64969 | 77.417506 | 72.893962 |
| Standard Dev | 2.692386607 | 6.385958128 | 2.082322916 | 11.31603612 |

TABLE 6

| | \multicolumn{4}{c}{Yield Force} | | | |
|---|---|---|---|---|
| | 14° | 30° | 44° | 90° |
| 1 | 40.88458 | 42.10942 | 50.83322 | 45.02627 |
| 2 | 41.70183 | 47.83502 | 52.1173 | 73.34027 |
| 3 | 36.94868 | 54.13914 | 54.31225 | 52.04165 |
| 4 | 37.83866 | 56.96712 | 49.41048 | 65.88202 |
| 5 | | 61.99002 | 50.55614 | 58.80218 |
| Average | 39.3434375 | 52.608144 | 51.445878 | 59.018478 |
| Standard Dev | 2.30480326 | 7.784120634 | 1.869272886 | 11.14368356 |

Discussion

The lack of reliable clinical solutions for SLIL injury contributes to a significant health burden. The paucity of regenerative medicine strategies in this area highlights the challenges of a Tissue Engineered Construct (TEC) for this type of reconstruction at both biological and biomechanical levels in order to attain successful incorporation. The scaffold developed in the present study was designed to increase regeneration using a cellular component with a mature extracellular matrix while addressing the biomechanical requirements by manufacturing a construct capable of withstanding physiological loading.

This study features the development of a multiphasic BLB multiphasic construct, combining additive manufacturing and cell sheet technology for the reconstruction of the dorsal SLIL. The potential utilisation of this scaffold strongly aligns with clinical practice as reconstruction procedures aim to replace the dorsal segment of the SLIL, the main contributor to carpal stability. Furthermore, using a tissue engineering approach as a replacement for grafts mitigates the issue of donor site morbidity. The clinical translatability and broader number of patients that could benefit from this novel approach justifies the creation and utilisation of a synthetic BLB scaffold.

Despite a plethora of studies aiming to develop TECs for other orthopaedic applications, there is a paucity of application of tissue engineering for the regeneration of bone, ligament and tendon in the hand and wrist highlighting the challenges present in this particular area. Decellularised cadaveric allografts of the proximal interphalangeal joint collateral ligament have limitations including graft availability, differences in the anatomical dimensions and potential disease transmission. In addition, the regenerative performance and re-cellularisation ability of such allografts are not known.

The implantation of cells within a mature ECM network, developed during in vitro culture, can significantly circumvent limitations related to host cell infiltration and differentiation within the construct. Cell sheet technology is an efficient manner to deliver cells committed towards a specific differentiation lineage by a prolonged in vitro maturation step whereby the deposition of the cell's own extracellular matrix improves the quality of the regenerated tissue. This study showed a significant remodelling of the cell sheet in the early period of the implantation, featuring a cell death peak at 3 days post-implantation concomitant with an increase in neutrophil infiltration followed by collagen densification at a later stage, consistent with tissue maturation. In addition, the presence of implanted cells gradually diminished in the tissue engineered graft while the total cell number increased at 28 days post-surgery suggesting infiltration of new cells at this more advanced healing stage. This indicates that the cells participated actively in both the recruitment of host cells and the creation of a suitable ECM template necessary for graft maturation and healing to take place. Similarly, ectopic implantation of our BLB construct revealed full tissue colonisation as early as 2 weeks post implantation, which was subsequently followed by significant maturation of the cell sheet as demonstrated by the increase in tissue alignment within the ligament compartment. Hence, it is reasonable to hypothesise that the cell sheets exerted similar roles; that is, both chemotactic and cell instructive via the ECM constituents.

In addition to the presence of cell sheets, the design of the scaffold demonstrated tissue-guiding properties, as shown by the slight increase in tissue alignment within the ligament compartment for the specimen without cell sheets. As shown here, the architecture of the scaffold plays a significant role in guiding tissue regeneration. Indeed, the development of advanced scaffold manufacturing technologies has enabled the fabrication of complex multiphasic scaffolds whereby the internal porous organisation can be controlled and tailored to address tissue-specific needs. Traditionally, the compartments of these multiphase scaffolds are fabricated separately and subsequently assembled using various methodologies. This may result in weak cohesion at the interface of the different compartments and affect the ability of the multiphasic construct to withstand physiological loads without excessive biomechanical fatigue. In the present strategy, the bone and ligament compartments are created via a continuous additive manufacturing process enabling the formation of a porous yet fully integrated interface. This strategy ensures that the polymeric filaments of the ligament compartment are entirely anchored in the adjacent layers of the bone compartment, allowing a high number of fusion points and thus providing excellent biomechanical stability. This was best illustrated by the ability of the BLB scaffold to withstand repetitive loads without excessive fatigue or delamination at the bone-ligament interface under repeated mechanical cycles. Another important aspect of the BLB design originates from the creation of a porous interface between the compartments resulting from the continuous printing, which had a significant impact on the integration of the ligament into the bone compartment. In the native ligament, the collagen fibres are transversely oriented and inserted into both the lunate and scaphoid bone enabling the transmission of force during flexion and torsion of the wrist. Such an organisation was partially observed in our construct with the formation of collagenous tissue aligned in the long axis of the BLB and inserted into the bone compartment. Although no direct insertion into the newly formed bone was observed due to the small volume of bone formed, these results illustrate the potential of the BLB construct to guide tissue regeneration in the ligament compartment while allowing cross-communication between the hard and soft tissues at the compartment interface.

This research has demonstrated that it is feasible to fabricate a multiphasic BLB scaffold using additive manufacturing for possible clinical application to reconstruct the dorsal SLIL after injury. Bone and ligament tissues were formed in their corresponding compartments with similar structural and mechanical properties to the native ligament in an animal model. The artificial scaffold may provide an alternative to current techniques for reconstruction of scapholunate instability.

Example Two: In Vivo Implantation and Characterization of a Novel 3D-Printed Multiphasic Scaffold in the Rabbit Knee for Scapholunate Ligament Reconstruction Overview (i) Aim Implantation of the multiphasic bone-ligament-bone (BLB) scaffold (which imitates the dorsal scapholunate interosseous ligament (SLIL)) into rabbits. The rabbit medial collateral ligament (MCL) has similar anatomical properties as the dorsal SLIL and thus, can be used as an animal model for testing this novel scaffold in vivo. This scaffold will facilitate regeneration of composite tissue and can be implanted for clinical use.

(ii) Methods

Multiphasic bone-ligament-bone scaffolds modeled from the dorsal component of the SLIL were 3D-printed with medical grade polycaprolactone (PCL). These simulated a BLB construct with two bone compartments bridged by aligned PCL fibres mimicking the architecture of the native ligament studied from cadaveric specimens. For surgical implantation, the native MCL of the rabbit was removed with holes drilled into insertion and origin points of the ligament on the femur and tibia using a 5 mm trephine. The bone compartments of the scaffold was press-fitted into the cavities and stapled in place. The rabbit knee joint was fixed in flexion using 1.4 mm K-wires for 4 weeks (n=9) prior to mobilization for an additional 4 weeks (n=9). In total, 18 samples were implanted into 18 rabbits and harvested at four and eight weeks. Mechanical tensile testing (n=5 per group) and in vivo characterization of the constructs were conducted.

(iii) Results

After 4 and 8 weeks in vivo, the scaffold remained intact. Mechanical testing of the BLB scaffolds showed that they were capable of withstanding normal SLIL physiological forces. After 4 weeks of mobilization of the knee joint, the scaffolds improved in strength. In vivo study in the rabbits demonstrated that the scaffold was biocompatible and displayed good tissue integration and vascularization. At 4 and 8 weeks, bone formation and ligament remodeling was observed in the corresponding compartments.

Materials and Methods (i) Clinical Translation Aim

A scaffold-only product was created that could be used for reconstruction (with adequate biomechanical properties)

TABLE 7

| (ii) Breakdown of study groups | | | |
|---|---|---|---|
| Treatment groups | uCT & Histology | Biomechanical testing | Total no. |
| Control (surgery + scaffold) | 3 | 5 | 8 |
| Total rabbits per timepoint | | | 9 |
| Timepoints = 2 | | | 16 (+2 as backup) |
| 4 weeks (immobilization, K-wire fixation) | | | |
| 8 weeks (+mobilization, K-wire removed) | | | |

(iii) Pre-Operative Care & Anaesthesia

1. The animals were anesthetized by intramuscular injection of Ketamine (35 mg/Kg) and Xylazine (5 mg/Kg) also using syringe with a 25 gauge needle. The rabbits were intubated during the surgical procedure.
2. Prophylactic antibiotic cover was provided prior to the surgery using subcutaneous injection of Kefzol® (cefazolin sodium) 20 mg/kg and Gentamicin 5 mg/kg using a syringe with a 25 gauge needle.
3. Pre-emptive analgesia was provided (meloxicam, 1 mg/kg, SC).
4. An antimuscarinic (glycopyrrolate, 0.004 mg/kg, IM) was administered prior to anaesthesia to reduce salivation, and risk of bradycardia.
5. Isofluorane 0.5-3% inhalant was used to maintain the anaesthesia throughout the surgery. Supplementary oxygen via a proper size nose cone and rodent-type breathing circuit was provided to the spontaneously breathing anesthetized rabbits in the proposed study. A nose cone suitable for rabbits was purchased via AAS (Advanced Anaesthesia Specialists), which was used specifically for this project.
6. A venous access (22 G angiocath) was established via the rabbits' marginal ear veins for administration of IV fluids during anaesthesia (if necessary). [2.5-5 mL saline/kg/hr using syringe pump]
7. Rabbits were positioned on a warming pad in order to maintain body temperature during the surgery.

(iv) Scaffold Preparation

Figure 22:
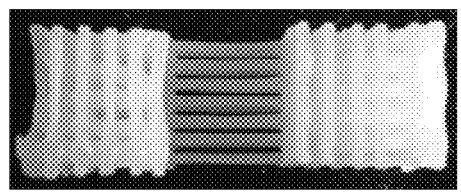
FIG. 22 provides images of multiphasic bone-ligament-bone scaffolds modeled from the dorsal component of the SLIL, as implanted into rabbits.
Figure 22:
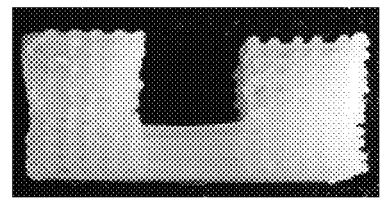

Rabbit scaffolds ligament compartment is 10 mm (elongation necessary to bridge knee joint) (FIG. 22).

Scaffold etching (To decrease hydrophobicity of PCL)

1. Place scaffolds in 5M NaOH at 37 degrees (water bath) for 30 mins.
2. Rinse with milliQ H2O until water penetrates scaffold easily
3. Place scaffolds on shaker plate and sit in water for 5 mins.
4. Discard and repeat until pH of water is ~7.

Scaffold sterilisation (night before)

1. Incubate scaffolds in 100% ethanol at RT for 30 mins.
2. Place scaffolds in wells with bone compartments touching bottom (forming upside down U) and place under UV light for 1 hour.
3. Leave under hood to evaporate overnight.

(v) Scaffold Assembly

Equipment Checklist

Falcon tube rack (to place sterile forceps)

Sterile forceps ×2

Scaffolds

Hystem-C Cell Culture Kit (Sigma-Aldrich)

Pipettes (1000 uL, 200 uL, 10 uL)+tips

Sterile eppendorf tubes

Sterile scalpel (to cut tips)

Roller/shaker plate (in main lab)

6 well plates (use for making/transporting loaded scaffolds)

Hystem Reconstitution

HA=670 uL degassed H2O (~700 uL excess)

Gelin=670 uL degassed H2O (~700 uL excess)

1. Vials were thawed to room temperature.
2. 700 uL of degassed H2O was added to Hystem-HA (silver? vial), vortxed and placed on roller for 30 mins.
3. 700 uL of degassed H2O was added to Gelin (blue vial), vortexed and placed on roller for 30 mins.
4. Contents of Gelin was added to HA. (NOTE: gel is very viscous, cut pipette tip when measuring)
5. 500 uL degassed H2O was added to crosslinker vial.

6. Vial was vortexed and placed on roller for 5-10 mins before use.
   1× scaffold (Control)
   HA+Gelin=40 uL (50 uL excess)
   Crosslinker=20 uL
   Ligament (50 ul)
   HA+Gelin=24 uL (34 uL excess)

Adding Gels to Scaffold

Figure 23:
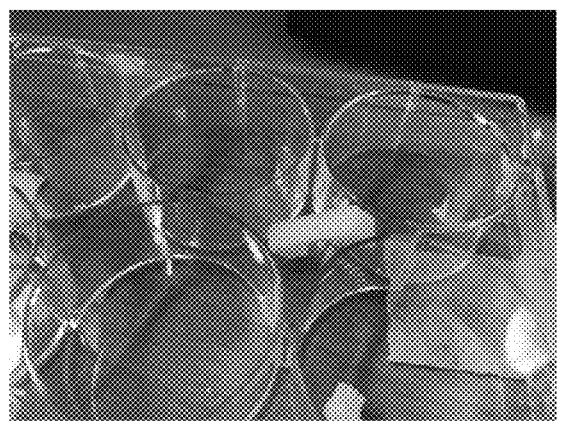
FIG. 23 is an image taken during multiphasic bone-ligament-bone scaffold preparation.
Figure 24:
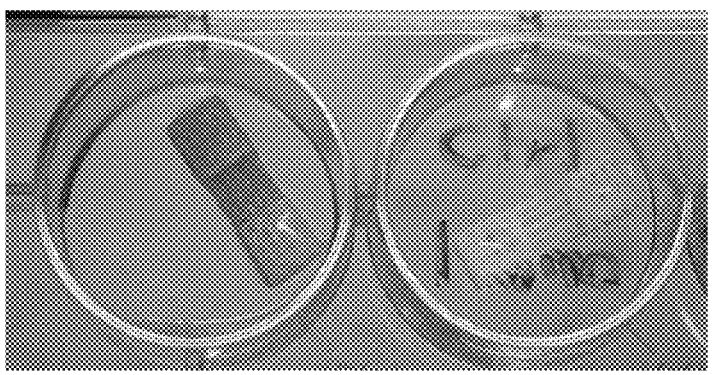
FIG. 24 is a further image taken during multiphasic bone-ligament-bone scaffold preparation.

1. Scaffold was removed from media and placed in dry well.
2. 200 uL pipette was used to suck out media from bone compartment.
3. 50 uL of control gel was dispensed in ligament compartment.
   a. 25 uL from bottom+top
4. 12.5 uL of control gel was dispersed at each bone-ligament interphase.
5. 40 uL of control gel was dispensed in cut 200 uL pipette tip (solution is very viscous) and up-down pipetting was used to push gel into bone compartment.
   a. Hold one bone plug with tweezer and dispense gel on top and 2× side of compartment
   b. Repeat for the other side
6. Place scaffolds tilted in between wells for 5 mins to crosslink (FIG. 23)
7. Set for 20-30 minutes flat on petri dish (implant in ~45 mins) (FIG. 24)

Figure 25:
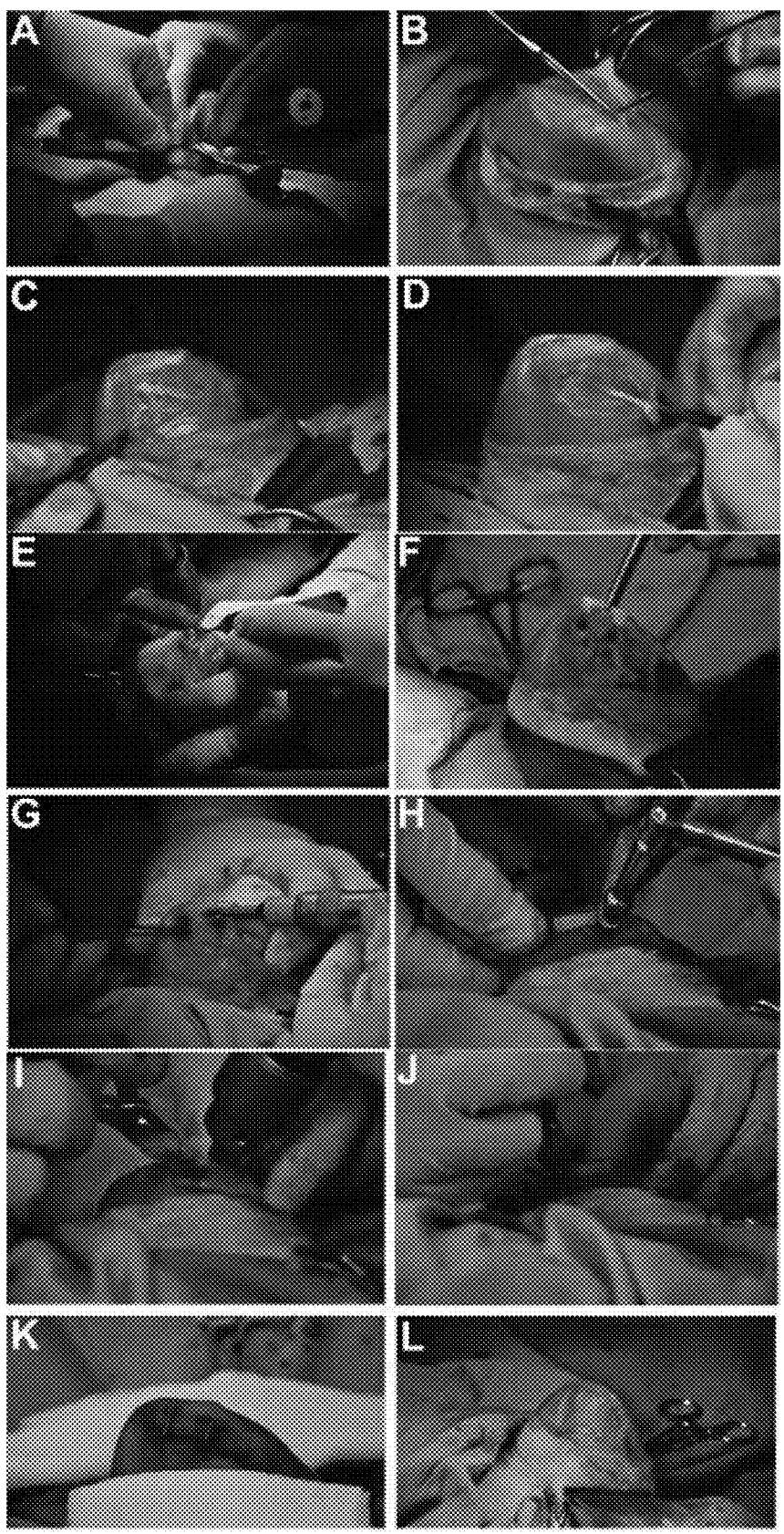
FIG. 25 provides a series of images showing surgical removal of native rabbit MCL and surgical implantation of the multiphasic bone-ligament-bone scaffold into the knee (A-L).

(vi) In Vivo Implantation (35 Rabbits, ~1-1.5 Hours)—Development of Novel Surgical Technique 1. With the rabbit placed in lateral recumbency, the medial aspect of the left knee joint was carefully shaved and disinfected with application of betadine solution. The right knee joint was also shaved to prevent hair contamination into the sterile field. Rabbit knee was in full flexion for implantation. Sterile drape was placed over rabbit and incision made over surgical field.
2. A superficial longitudinal incision (using 15-C blades) was made (in line with the patella position) to reflect the skin and expose the knee joint. Any superficial blood vessels in subsequent tissue layers were cauterized using diathermy. The retinaculum was then be incised, blunt dissected from the underlying muscle and carefully reflected.
3. K-wire fixation
   a. A 1.6 mm Kirshner wire was attached to the driver and inserted longitudinally from mid-shin on the tibia through to the femur to secure the knee joint in full flexion. (Tip: hold back soft tissue to prevent it getting caught on wire). The K wire was bent and hooked over the femur as well as bent on the tibial end to prevent wire pull out and restrict joint movement.
4. Native MCL was exposed and the proximal end will removed from the medial tubercle of the femur using a scalpel. MCL was left attached to the tibia so that the proximal end could be sutured down over the scaffold to further secure it after implantation (FIG. 25).
5. 5 mm trephine burr (Stryker ¼" drill) was used to drill one central cavity (Tip: start burr before coming in contact with bone otherwise the burr will slip off the surface) for fitting scaffold bone compartments in the femur medial tubercle at the site of MCL attachment. (NOTE: Ensure irrigation was used)
6. Template scaffold (was used to mark out point out location of the distal bone trough (close to distal attachment of MCL on tibia). 5 mm trephine burr was used to drill central cavity on tibia.
7. 1.8 mm round burs+4 mm oval burs was used to widen troughs superficially (shave down bone adjacent to knee joint) to press fit scaffold. Use elevators to protect menisci of knee joint. it was ensured that alignment of the scaffold is the same as that of the native MCL.
8. In vivo constructs were implanted into the knee joint by press-fitting the bone compartments into the drilled cavities. (Note: Avoid excessive handling of in vivo constructs)
9. Holes were drilled for staple placement (starting with smallest drill bit), depth=10 mm.
10. 2× 8 mm staples (positioned across each bone compartment) were press-fitted into drilled holes to fix the scaffold to the femur and tibia.
11. The retinaculum was pulled over to cover the scaffold and sutured with 4-0 vicryl monofilament using simple interrupted technique.
12. The skin was sutured with 4-0 vicryl monofilament sutures using simple interrupted/continuous suture technique.
13. Area was washed with saline and swabbed with betadine to disinfect the wound.

(vii) K-Wire Removal (4 Weeks)

1. Hair over surgery site was shaved and skin will be disinfected using antiseptic.
2. A small 1 cm incision was made over the femoral end of the K-wire.
3. K-wire was cut and removed using pliers.
4. Incision was sutured using 4.0 vicryl monofilament sutures.

(viii) Post-Operative Care

1. Upon completion of the surgery, to reverse the effects of xylazine and hasten recovery from anaesthesia, Antisedan® (atipamezole hydrochloride) (0.5-1 mg/kg, IM) will be administered to each rabbit.
2. The rabbits were monitored postoperatively until they are fully recovered, all the observations were recorded in the post-op monitoring sheets (attached). Full recovery was achieved when the rabbit regains its consciousness, neuromuscular conduction, and airway protective reflexes.
3. The rabbit was constantly monitored until the animal returns to an alert, responsive and conscious state, gag reflex returns, and the rabbit is ambulatory. The rabbits heart rate, respiratory rate and rhythm, capillary refill time (CRT), and mucous membrane colour was also constantly checked until the return to normal values.
4. Post-operative multi-modal analgesia was provided using a combination of opioid (buprenorphine, 0.05-0.1 mg/kg, q8-10 h, for up to 48 hours), tramadol (25 mg/lit, drinking water, for 5 days post-op), meloxicam (1 mg/kg, oral, for 2 days post-op).
5. Post-operative antibiotics was administered for the first 5 days after surgery.
6. Wound healing was monitored by inspection for any signs of inflammation such as redness or pus at the operation site during post-operative and long term checks. Stitches were monitored to ensure full wound closure.

(ix) Euthanasia & Sample Recovery (4 & 8 Weeks)

1. 36 animals were euthanized by intravenous injection of pentobarbital sodium (150 mg/kg of Lethabarb, 25 G needle) at the 4 & 8 week timepoint.
2. K-wires were removed from samples.
3. Knee joint (containing sample) was extracted and fixed in paraformaldehyde.

Results

Figure 26:
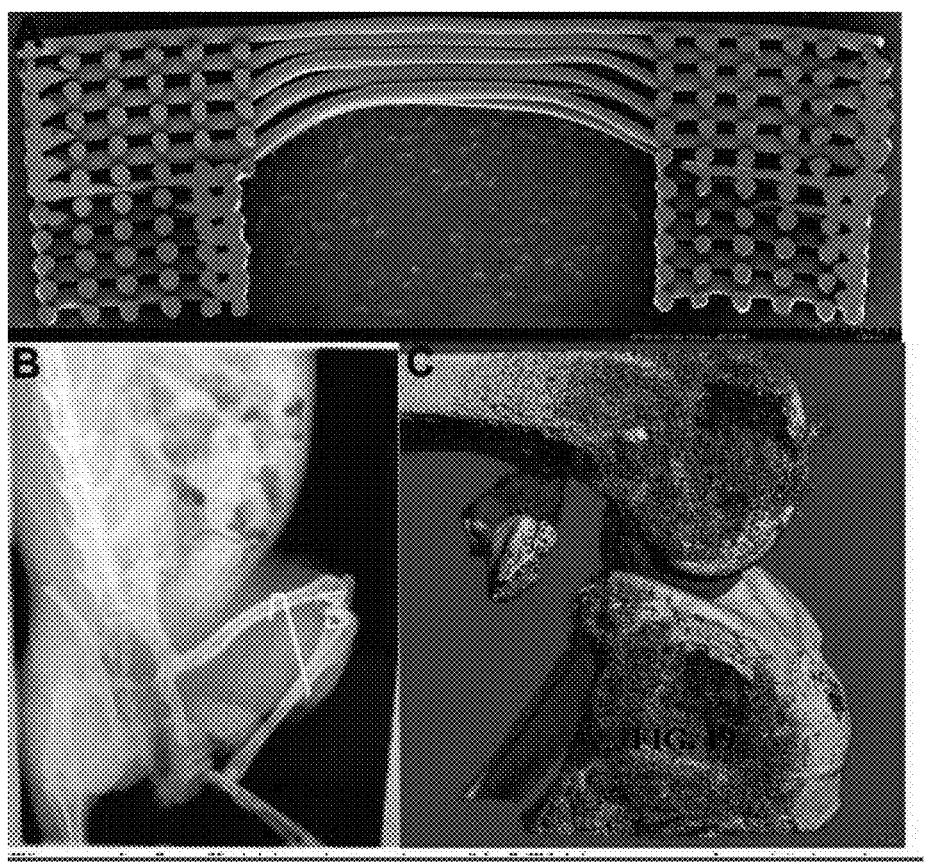
FIG. 26 provides images showing scaffold implantation, fixation of the knee joint and bone mineralization. A) SEM images of multiphasic scaffold showing bone-ligament-bone compartments. B) X-ray showing K-wire fixation of the rabbit knee joint in flexion. C) MicroCT reconstructions illustrating new bone mineralization in the femur and tibia after 4 weeks.
Figure 27:
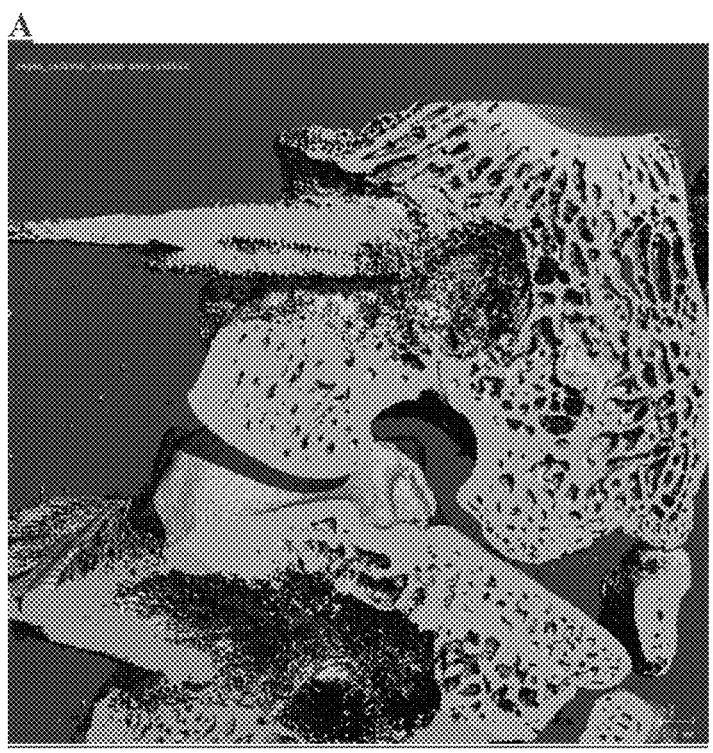
FIG. 27 provides images showing MicroCT results of bone regeneration in the MCL joint of a rabbit implanted with a multiphasic bone-ligament-bone scaffold. A) 4 weeks. B) and C) 8 weeks.
Figure 27:
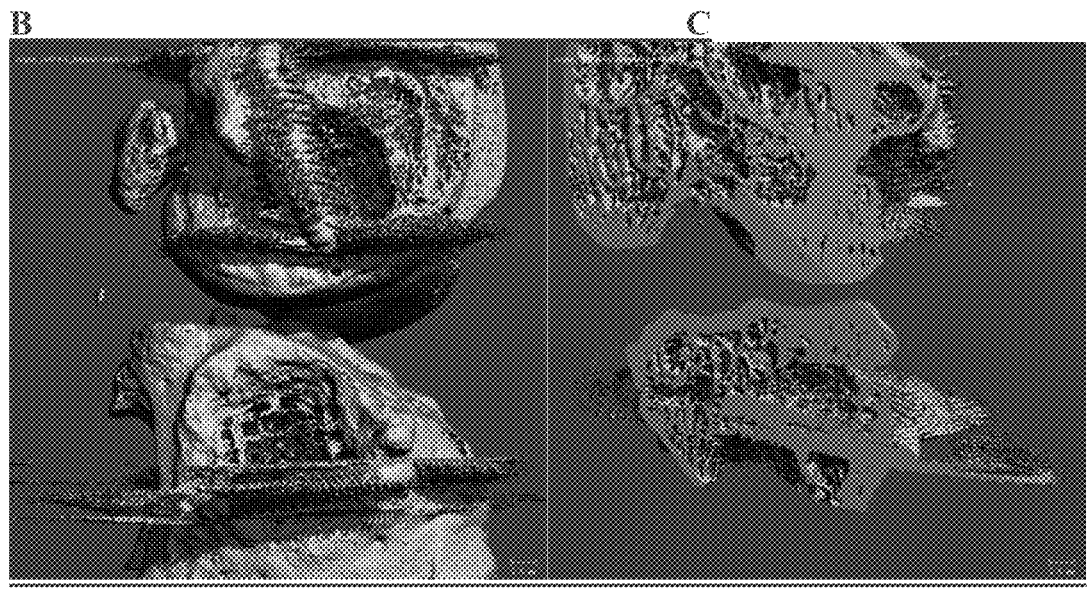

FIG. 26 demonstrates new bone mineralization in a rabbit knee joint (MCL removed and multiphasic bone-ligament-bone scaffold implanted) under K-wire fixation. FIG. 27 further demonstrates bone regeneration/mineralisation in the joint at 4 and 8 weeks.

Figure 28:
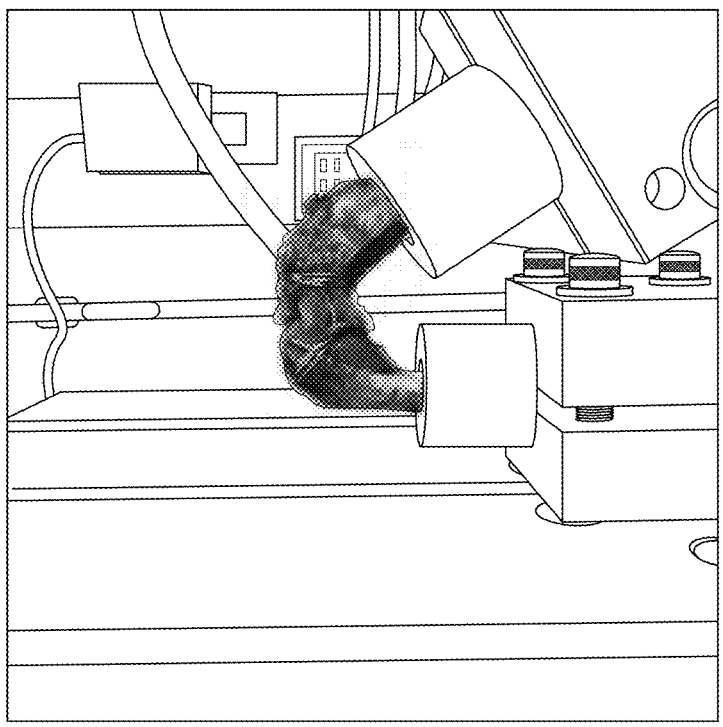
FIG. 28 provides an image of an apparatus used for biomechanical testing of bone-ligament-bone constructs generated using the multiphasic bone-ligament-bone scaffold.
Figure 29:
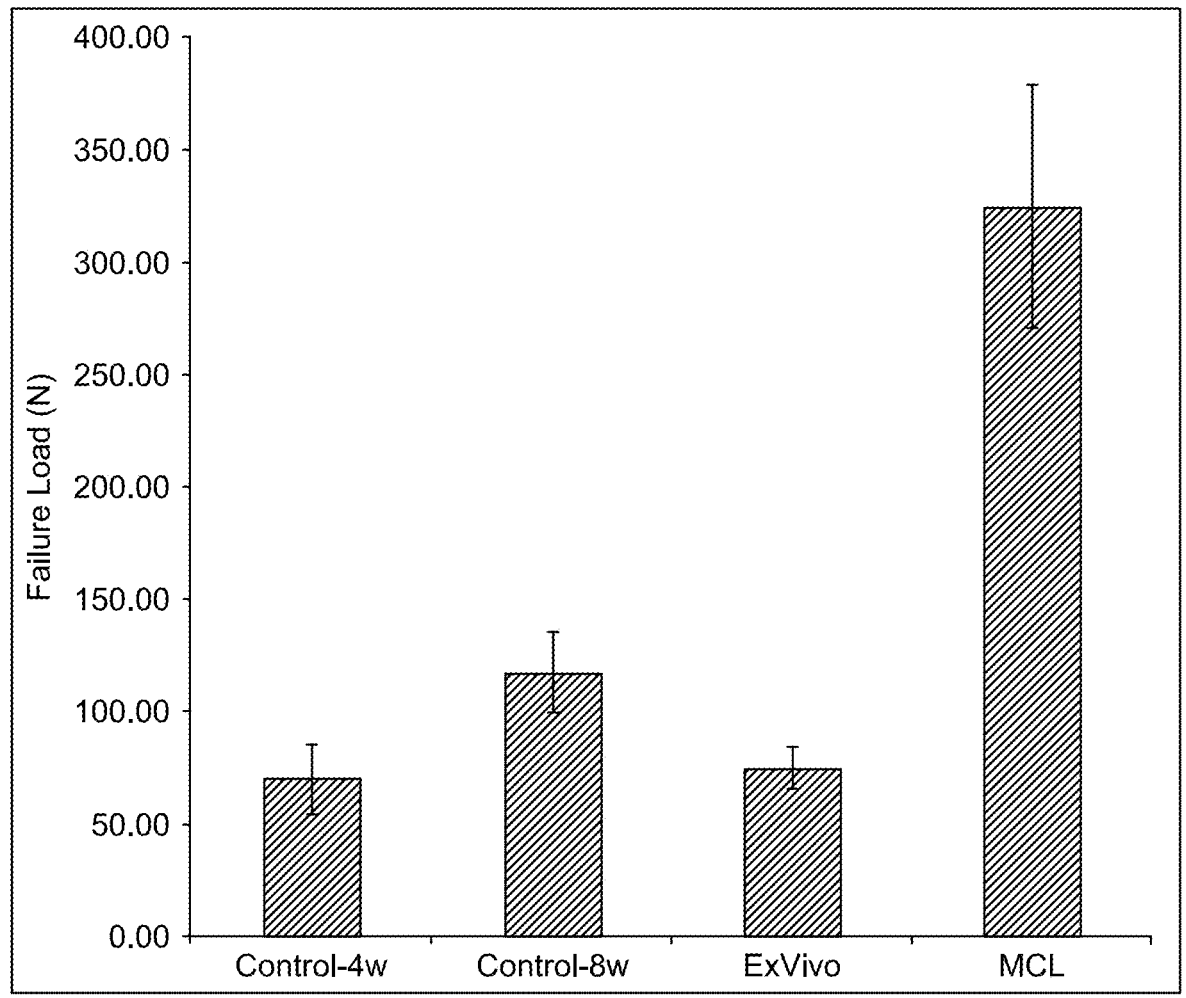
FIG. 29 is a graph showing mechanical strength measurements derived from the tensile testing of bone-ligament-bone constructs at 4 and 8 weeks.

Biomechanical testing showed that when comparing the scaffolds at 4 and 8 weeks, the mechanical strength in tensile testing increased significantly over the time period. (FIGS. 28 and 29).

Figure 30:
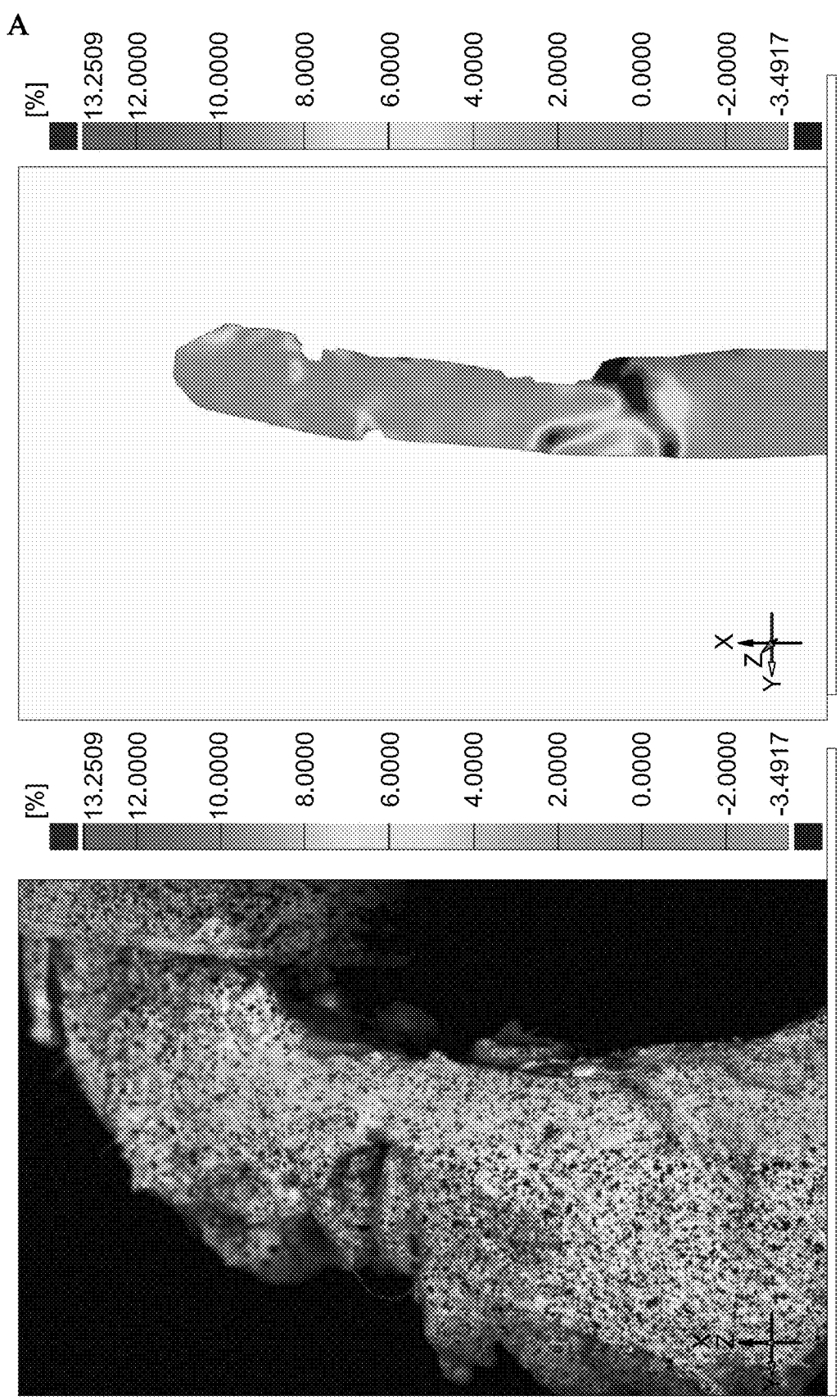
FIG. 30 shows strain maps generated from (A) native rabbit knee joints and (B) rabbit knee joints with MCL removed and replaced with multiphasic bone-ligament-bone scaffolds.
Figure 30:
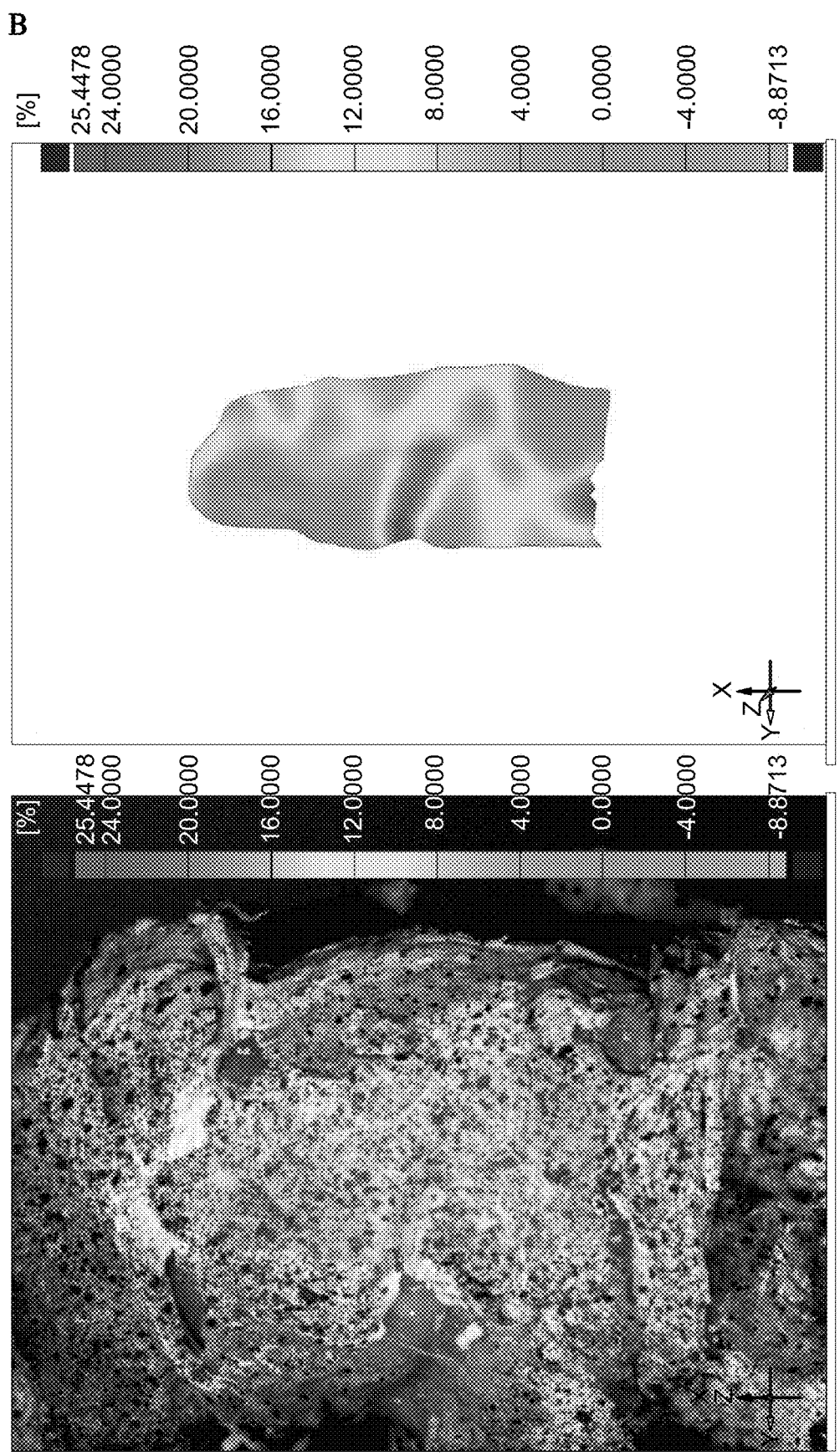

Strain maps (FIG. 30) illustrate that the native MCL had much more concentrated regions of increased strain. This can be compared to the strain map of the control scaffold which distributed the force over a larger surface area. The failure point for the control scaffold is within the ligament compartment compared to that of the native MCL at the bone-ligament interphase. This suggests that the bone-ligament interphase of the scaffold is strong enough to withstand considerable force.

Figure 31:
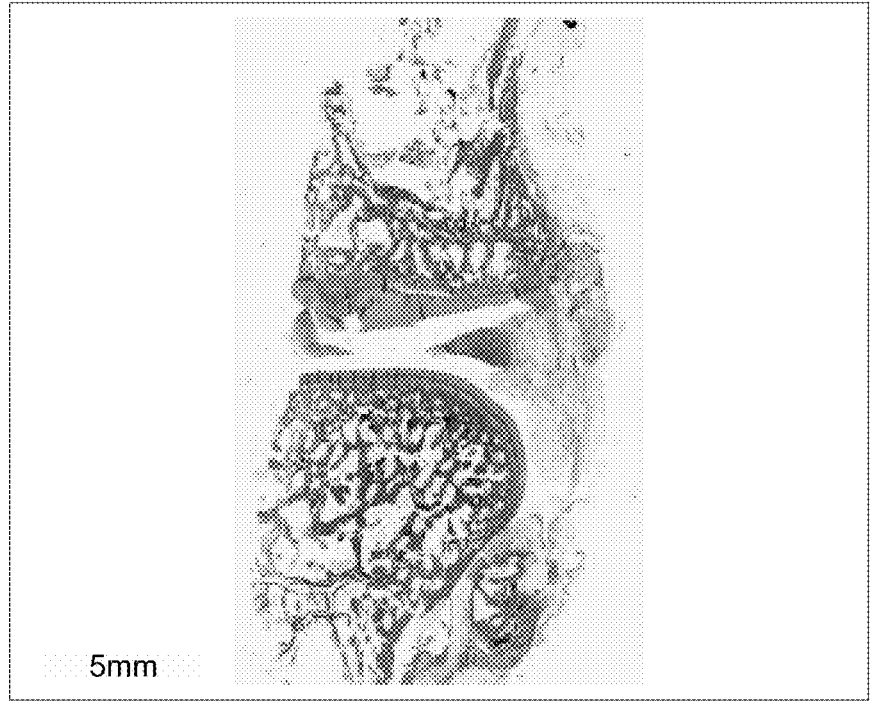
FIG. 31 shows histology images (haematoxylin and eosin staining) of rabbit medial collateral ligaments (knee): A) Native MCL ligament ('276 native'). B) Normal rabbit MCL architecture. C) control samples 4 weeks ('336 Ctrl') Full scaffold in vivo showing intact ligament fibres traversing between bone compartments. D) Bone Compartment Bone mineralisation around PCL struts. E) Ligament Compartment 2λ. F) Ligament compartment 10× (some aligned fibres). G) 8 weeks ('241 Ctrl') Full scaffold in vivo showing intact ligament fibres traversing between bone compartments. H) More bone mineralisation around PCL struts observed at 8 W when compared to 4 W. I) Ligament compartment 2×. J) Ligament compartment 10× (more aligned fibres).
Figure 31:
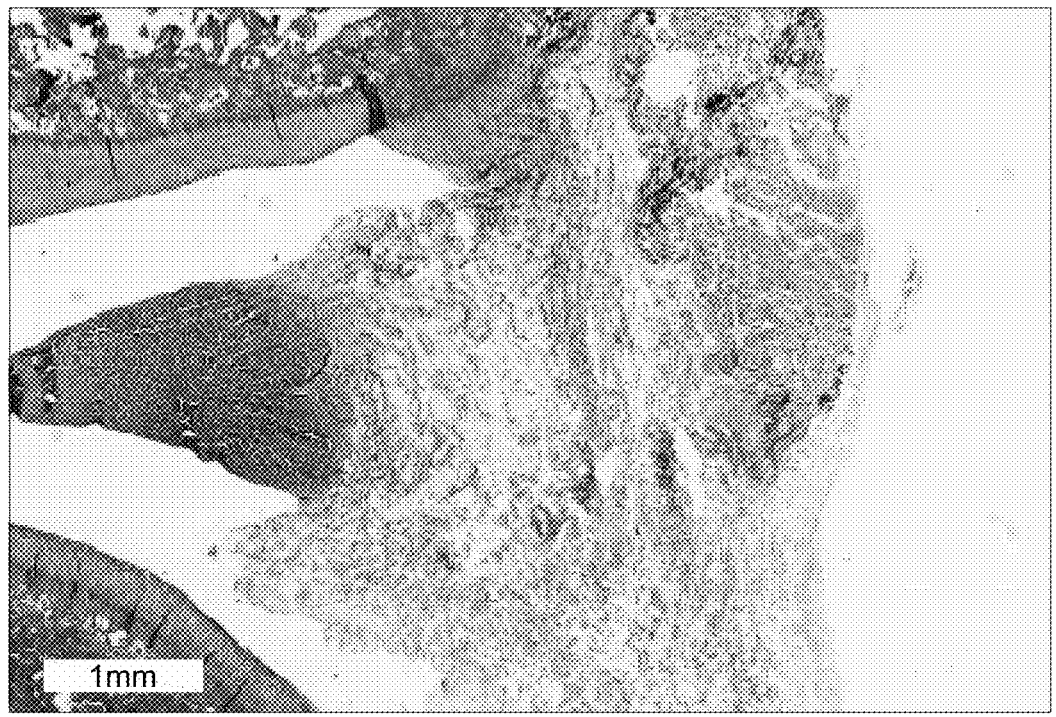
Figure 31:
Figure 31:
Figure 31:
Figure 31:
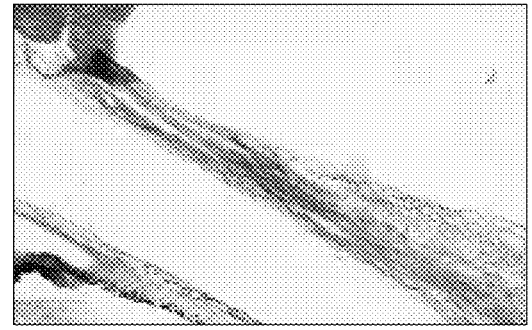
Figure 31:
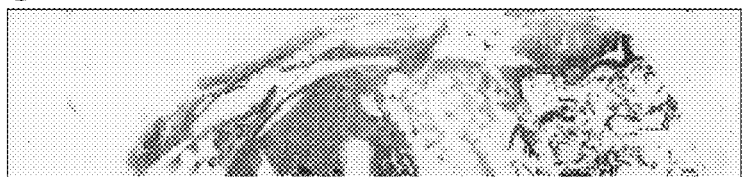
Figure 31:
Figure 31:
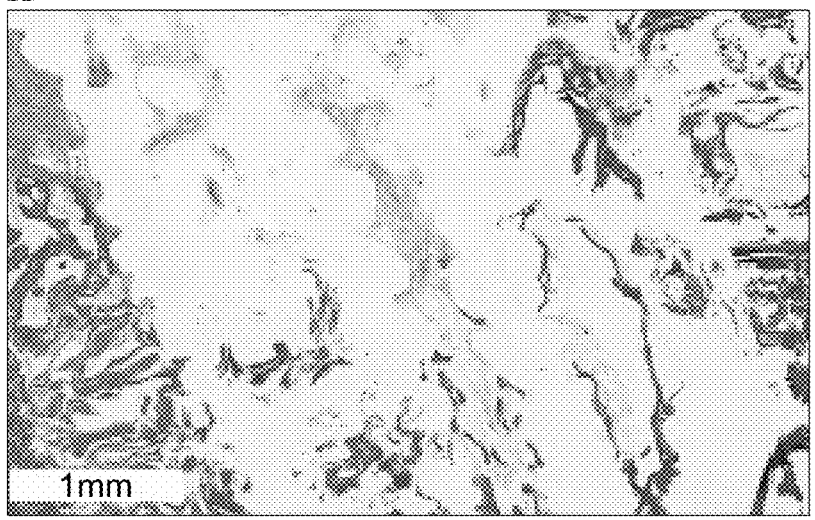
Figure 31:
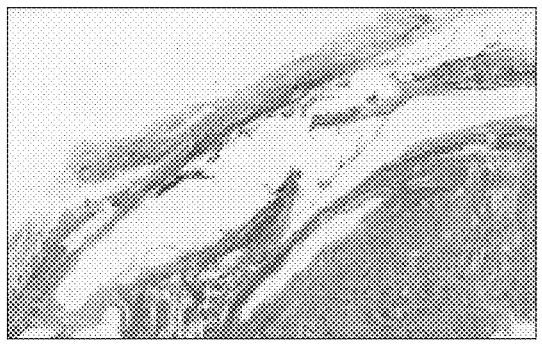
Figure 31:
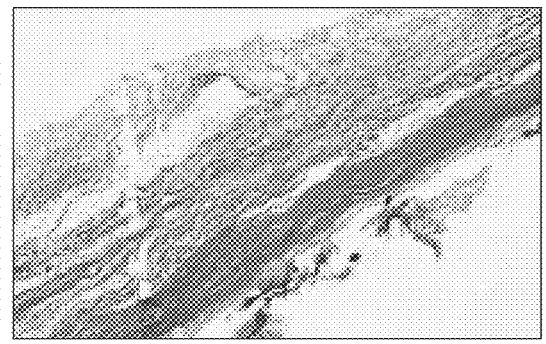

Histology results are shown in FIG. 31.
A. Native MCL Ligament (276 'native')
B. Normal rabbit MCL architecture
C. CONTROL Samples 4 WEEKS ('336 Ctrl') Full scaffold in vivo showing intact ligament fibres traversing between bone compartments
D. Bone Compartment Bone mineralisation around PCL struts
E. Ligament Compartment 2×
F. Ligament compartment 10× (some aligned fibres)
G. 8 WEEKS ('241 Ctrl') Full scaffold in vivo showing intact ligament fibres traversing between bone compartments
H. More bone mineralisation around PCL struts observed at 8 W when compared to 4 W
I. Ligament compartment 2×
J. Ligament compartment 10× (more aligned fibres)

The histology results support the microCT data. Samples:
Did not have ectopic bone formation at 4 weeks or 8 weeks
Showed more bone mineralisation in bone compartments noted around PCL struts at 8 weeks compared to 4 weeks
Showed more ligament alignment noted in ligament compartment at 8 weeks compared to 4 weeks
In a challenging model, with higher biomechanical forces than that found normal movements of the wrist, the scaffold did not fail at 8 weeks.

The invention claimed is:

1. A three-dimensional multiphasic synthetic tissue scaffold comprising first, second and third compartments, wherein:
   each said compartment comprises distinct microstructural, chemical, or mechanical properties, and is connected with at least one other compartment of the scaffold via a continuous interface;
   the tissue scaffold is porous; and
   the external morphology of the tissue scaffold mimics that of a mammalian joint or a component thereof;
   wherein any one or more of the first, second and/or third compartments comprises:
      a series of fibres; or
      a series of fibers comprising multiple fibre layers
   wherein the second compartment comprises a series of fibres mimicking the external morphology of a series of ligaments, and said series of fibres are located intermediate to and connecting the first and third compartments; and wherein:
      the series of fibres in the second compartment comprise first and second fibre layers,
      the first fibre layer is aligned along a first axis,
      the second fibre layer is aligned along a second axis, and
      the second axis is rotated at an angle relative to the first axis.

2. The multiphasic synthetic tissue scaffold of claim 1, wherein the second axis is rotated by an angle of:
   at least: 2°, 3°, 4°, 5°, 6°, 7°, 8°, 9°, 10°, 11°, 12°, 13°, 14°, 15°, 16°, 17°, 18°, 19°, or 20° relative to the first axis; or
   between 20° and 50°, between 25° and 45°, between 30° and 40°, between 25° and 35°, or about 35°, relative to the first axis.

3. The multiphasic synthetic tissue scaffold of claim 1, wherein the multiple fibre layers comprise a third layer aligned along a third axis, and the third axis is:
   rotated at an angle relative to either or both of the first axis and/or second axis; or
   rotated at an equal or substantially equal angle relative to either or both of the first axis and second axis; or
   rotated in an anticlockwise direction relative to the first axis, and rotated in a clockwise direction relative to the second axis.

4. The multiphasic synthetic tissue scaffold of claim 1, wherein:
   the external morphology of each of the first and third compartments mimics that of a bone, and the external morphology of the second compartment mimics that of a series of ligaments located intermediate to and connecting the first and third compartments; or
   the external morphology of the tissue scaffold mimics that of a scapholunate joint or a component thereof, or
   the external morphology of the first compartment mimics that of a scaphoid, the external morphology of the third compartment mimics that of a lunate, and the external morphology of the second compartment mimics that of a series of scapholunate ligaments.

5. The multiphasic synthetic tissue scaffold of claim 4, wherein the series of scapholunate ligaments are dorsal scapholunate ligaments, and are not proximal or palmar scapholunate ligaments.

6. The multiphasic synthetic tissue scaffold of claim 1, wherein the scaffold comprises pores with a maximum width of between 100 µM and 1000 µM, between 100 µM and 1000 µM, between 100 µM and 800 µM, between 100 µM and 600 µM, between 200 µM and 600 µM, between 200 µM and 500 µM, between 300 µM and 600 µM, between 300 µM and 500 µM, between 350 µM and 600 µM, between 350 µM and 500 µM, between 400 µM and 600 µM, or between 400 µM and 500 µM.

7. The multiphasic synthetic tissue scaffold of claim 1, further comprising:
   mammalian cells;
   mammalian cells are selected from the group consisting of: ligament-derived stem cells, cartilage stem cells, mesenchymal stem cells (bone marrow stromal cells), adipose-derived stromal cells (e.g. bone-marrow derived mesenchymal stem cells, adipose-derived mesenchymal stem cells), osteoblasts, osteoblast-like cells, stem cells, progenitor cells, or any combination thereof;
   human mesenchymal stem cells, or human bone marrow mesenchymal stem cells.

8. The multiphasic synthetic tissue scaffold of claim 7, wherein the mammalian cells are within a cell sheet wrapped around and/or inserted into one or more of the compartments.

9. The multiphasic synthetic tissue scaffold of claim 1, wherein any one or more of the first, second and/or third compartments comprises:
   a polymeric material; or
   a polymeric material is selected from the group consisting of: collagen, chitosan, hyaluronic acid, alginate, gelatin, polyethylene glycol dimethacrylate (PEG), gelatin methacryloyl, matrigel, fibrinogen, agarose, polyurethane, and polycaprolactone.

10. The multiphasic synthetic tissue scaffold of claim 9, wherein the polymeric material is polyurethane.

11. The multiphasic synthetic tissue scaffold of claim 1, wherein the tissue scaffold is produced using a three-dimensional (3D) bioprinter to continuously deposit the polymeric material onto a platform until the tissue scaffold is produced in its entirety.

12. The multiphasic synthetic tissue scaffold of claim 1, wherein the continuous interface is porous.

13. A method for producing the three dimensional multiphasic synthetic tissue scaffold of claim 1, the method comprising using a three-dimensional (3D) bioprinter to continuously deposit polymeric material onto a platform until the tissue scaffold is produced in its entirety.

14. A method for treating an injured ligament in a subject, the method comprising transplanting the three dimensional multiphasic synthetic tissue scaffold of claim 1 into a body compartment of the subject comprising the injured ligament.

15. The method of claim 14, wherein the body compartment is a joint.

16. The method of claim 14, wherein the joint is a scapholunate joint and the ligament is a scapholunate interosseous ligament (SLIL) or a mammalian equivalent thereof.

17. The method of claim 14, wherein the subject is a human.

* * * * *